(12) United States Patent
Alvaro et al.

(10) Patent No.: US 7,276,509 B2
(45) Date of Patent: Oct. 2, 2007

(54) PIPERIDINE DERIVATIVES AND THEIR USE AS ANTAGONISTS OF TACHYKININS

(75) Inventors: Giuseppe Alvaro, Verona (IT); Romano Di Fabio, Verona (IT)

(73) Assignee: Glaxo Group Limited (GB)

( * ) Notice: Subject to any disclaimer, the term of this patent is extended or adjusted under 35 U.S.C. 154(b) by 406 days.

(21) Appl. No.: 10/502,261

(22) PCT Filed: Feb. 5, 2003

(86) PCT No.: PCT/GB03/00501

§ 371 (c)(1),
(2), (4) Date: Jul. 22, 2004

(87) PCT Pub. No.: WO03/066621

PCT Pub. Date: Aug. 14, 2003

(65) Prior Publication Data

US 2005/0096313 A1    May 5, 2005

(30) Foreign Application Priority Data

Feb. 8, 2002  (GB) ................. 0203022.9

(51) Int. Cl.
*A61K 31/496* (2006.01)
*C07D 401/04* (2006.01)
*C07D 211/58* (2006.01)
(52) U.S. Cl. ................. 514/253.13; 544/360
(58) Field of Classification Search ............... 544/360; 514/253.13
See application file for complete search history.

(56) References Cited

U.S. PATENT DOCUMENTS

| | | | |
|---|---|---|---|
| 4,087,424 A | 5/1978 | Saikawa et al. |
| 4,110,327 A | 8/1978 | Saikawa et al. |
| 4,112,090 A | 9/1978 | Saikawa et al. |
| 4,219,554 A | 8/1980 | Saikawa et al. |
| 4,308,387 A | 12/1981 | Bjork et al. |
| 4,327,097 A | 4/1982 | Saikawa et al. |
| 4,379,152 A | 4/1983 | Saikawa et al. |
| 4,410,522 A | 10/1983 | Saikawa et al. |
| 5,028,610 A | 7/1991 | Hirai et al. |
| 5,109,014 A | 4/1992 | Jacobson et al. |
| 5,334,606 A | 8/1994 | MacLeod et al. |
| 5,348,955 A | 9/1994 | Greenlee et al. |
| 5,360,820 A | 11/1994 | Hagan et al. |
| 5,464,788 A | 11/1995 | Bock et al. |
| 5,538,982 A | 7/1996 | Hagan et al. |
| 5,563,127 A | 10/1996 | Amparo et al. |
| 5,576,317 A | 11/1996 | Gonsalves et al. |
| 5,696,123 A | 12/1997 | Dollinger et al. |
| 5,698,538 A | 12/1997 | Amparo et al. |
| 5,708,006 A | 1/1998 | Dollinger et al. |
| 5,710,169 A | 1/1998 | Russell et al. |
| 5,716,942 A | 2/1998 | Dorn et al. |
| 5,756,504 A | 5/1998 | Bock et al. |
| 5,814,636 A | 9/1998 | Katano et al. |
| 5,859,015 A | 1/1999 | Graham et al. |
| 5,883,096 A | 3/1999 | Lowe et al. |

(Continued)

FOREIGN PATENT DOCUMENTS

DE    2519400    4/1978

(Continued)

OTHER PUBLICATIONS

Vippagunta et al. Advanced Drug Delivery Reviews, vol. 48, pp. 3-26 (2001).*

(Continued)

*Primary Examiner*—Emily Bernhardt
(74) *Attorney, Agent, or Firm*—Lorie Ann Morgan

(57) ABSTRACT

The present invention relates to piperidine derivatives of formula (I):

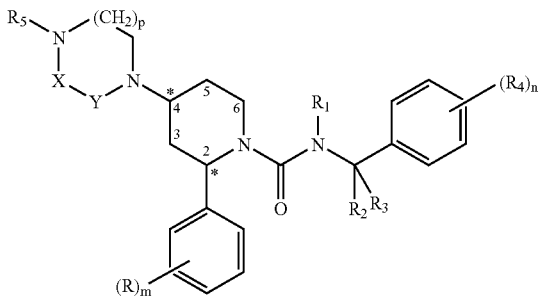

wherein
R represents halogen or $C_{1-4}$ alkyl;
$R_1$ represents hydrogen or $C_{1-4}$ alkyl;
$R_2$ represents hydrogen, $C_{1-4}$ alkyl;
$R_3$ represents hydrogen, $C_{1-4}$ alkyl;
$R_4$ represents trifluoromethyl, $C_{1-4}$ alkyl, $C_{1-4}$ alkoxy, trifluoromethoxy or halogen;
$R_5$ represents hydrogen, $C_{1-4}$ alkyl, $C_{3-7}$ cycloalkyl, $C(O)R_6$ or $S(O)_2R_6$;
$R_6$ represents $C_{1-4}$ alkyl or $C_{3-7}$ cycloalkyl;
m is zero or an integer from 1 to 3;
n is an integer from 1 to 3;
p is an integer from 1 to 2;
X and Y are independently C(O) or $CH_2$;
provided that
i) X and Y are not both C(O) and
ii) when X and Y are both $CH_2$ and p is 1, $R_5$ is not hydrogen, $C_{1-4}$ alkyl or $C(O)R_6$;
and pharmaceutically acceptable salts and solvates thereof, the process for their preparation and their use in the treatment of conditions mediated by tachykinins.

23 Claims, No Drawings

U.S. PATENT DOCUMENTS

| | | | |
|---|---|---|---|
| 5,935,951 A | 8/1999 | Ofner et al. | |
| 5,952,315 A | 9/1999 | Baker et al. | |
| 5,977,104 A | 11/1999 | Baker et al. | |
| 5,985,881 A | 11/1999 | Dollinger et al. | |
| 5,998,444 A | 12/1999 | Russell et al. | |
| 6,037,352 A | 3/2000 | Lowe et al. | |
| 6,057,323 A | 5/2000 | Zhang et al. | |
| 6,090,807 A | 7/2000 | Hellendahl et al. | |
| 6,114,315 A | 9/2000 | Baker et al. | |
| 6,117,855 A | 9/2000 | Carlson et al. | |
| 6,147,083 A | 11/2000 | Russell et al. | |
| 6,191,135 B1 | 2/2001 | Dollinger et al. | |
| 6,191,139 B1 | 2/2001 | Hagan et al. | |
| 6,197,772 B1 | 3/2001 | Janssens et al. | |
| 6,235,732 B1 | 5/2001 | Dollinger et al. | |
| 6,288,068 B1 | 9/2001 | Lowe et al. | |
| 6,319,953 B1 | 11/2001 | Carlson et al. | |
| RE37,886 E | 10/2002 | Janssens et al. | |
| 6,521,621 B1 | 2/2003 | Janssens et al. | |
| 6,642,240 B2 | 11/2003 | Alvaro et al. | |
| 2002/0103205 A1 | 8/2002 | Lowe et al. | |

FOREIGN PATENT DOCUMENTS

| | | |
|---|---|---|
| EP | 287734 | 10/1987 |
| EP | 293532 | 10/1987 |
| EP | 0655442 | 5/1995 |
| EP | 718287 | 12/1995 |
| EP | 0721941 | 7/1996 |
| GB | 1508062 | 4/1975 |
| JP | 57/118587 | 7/1982 |
| WO | WO92/16211 | 10/1992 |
| WO | WO95/00498 | 1/1995 |
| WO | WO95/25443 | 9/1995 |
| WO | WO96/02503 | 2/1996 |
| WO | WO96/03378 | 2/1996 |
| WO | WO96/10562 | 4/1996 |
| WO | WO96/14844 | 5/1996 |
| WO | WO96/20173 | 7/1996 |
| WO | WO97/16440 | 5/1997 |
| WO | WO97/32865 | 9/1997 |
| WO | WO97/36592 | 10/1997 |
| WO | WO97/36593 | 10/1997 |
| WO | WO97/36888 | 10/1997 |
| WO | WO97/36889 | 10/1997 |
| WO | WO98/01133 | 1/1998 |
| WO | WO98/20001 | 5/1998 |
| WO | WO98/57954 | 12/1998 |
| WO | WO99/09985 | 3/1999 |
| WO | WO99/26921 | 6/1999 |
| WO | WO 01/25219 | 4/2001 |
| WO | WO 02/00631 | 1/2002 |
| WO | WO 02/32867 | 4/2002 |
| WO | WO 02/055518 | 7/2002 |
| WO | WO 02/057233 | 7/2002 |
| WO | WO 03/099787 | 12/2003 |
| WO | WO 2004/033428 | 4/2004 |

OTHER PUBLICATIONS

Ohnmacht et al. Annual Reports in Medicinal Chemistry, vol. 33, p. 71-80 (1998).*

Davis, David T., "Synthesis A. Biological Activity of a Series of Piperazin-2, 3-Biones," Journal of Antibiotics, vol. XLII, No. 3, 1989, pp. 367-373.

Rupniak et al. "Differential inhibition of foot tapping and chromodacyorrhoea in gerbils by CNS penetrant and non-penetrant tachykinin NK, receptor antagonists." European Journal of Pharmacology 265:179-183 (1994).

Megens, A., et al. J. Pharmacology and Experimental Therapeutics 302(2):696-709 (2002).

Challet, E., et al. Neuropharmacology 40(3):408-415 (2001).

Romerio, et al. Clinical Pharmacology and Therapeutics 66(5):522-527 (1999).

Pacher, P., et al. "Review of Cardiovascular Effects of Fluoxetine, A Selective Serotonine Reuptake Inhibitor, Compared to Tricyclic Antidepressants." Current Medicinal Chemistry, 5, 381-390, 1998.

* cited by examiner

PIPERIDINE DERIVATIVES AND THEIR USE AS ANTAGONISTS OF TACHYKININS

CROSS REFERENCES TO RELATED APPLICATIONS

This application is a 371 Application of PCT/GB03/00501, filed 5 Feb. 2003, which claims priority to GB Application Ser. No. 0203022.9, filed 8 Feb. 2002.

The present invention relates to C-aryl piperidine derivatives, to processes for their preparation, to pharmaceutical compositions containing them and to their medical use.

In particular the invention relates to novel compounds which are potent and specific antagonists of tachykinins, including substance P and other neurokinins.

WO 99/37304 discloses inter alia some 2-aryl-1,4-disubstituted piperidine derivatives as factor Xa inhibitors. Such compounds are useful as inhibitors of blood coagulation in mammalian species.

WO 97/16440 and WO 02/32867 disclose certain 2-aryl 1,4-disubstituted piperidine derivatives as NK1 antagonists.

However, in the above cited documents there is neither disclosure nor suggestion of any compound as claimed herein.

Thus, the present invention provides compounds of formula (I)

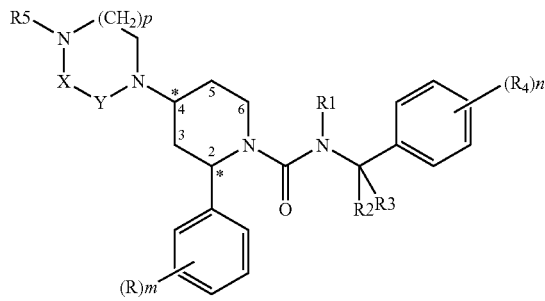

(I)

wherein
R represents halogen or $C_{1-4}$ alkyl;
$R_1$ represents hydrogen or $C_{1-4}$ alkyl;
$R_2$ represents hydrogen, $C_{1-4}$ alkyl;
$R_3$ represents hydrogen, $C_{1-4}$ alkyl;
$R_4$ represents trifluoromethyl, $C_{1-4}$ alkyl, $C_{1-4}$ alkoxy, trifluoromethoxy or halogen;
$R_5$ represents hydrogen, $C_{1-4}$ alkyl, $C_{3-7}$ cycloalkyl, $C(O)R_6$ or $S(O)_2R_6$;
$R_6$ represents $C_{1-4}$ alkyl or $C_{3-7}$ cycloalkyl;
m is zero or an integer from 1 to 3;
n is an integer from 1 to 3;
p is an integer from 1 to 2;
X and Y are independently C(O) or $CH_2$;

provided that
i) X and Y are not both C(O) and
ii) when X and Y are both $CH_2$ and p is 1, $R_5$ is not hydrogen, $C_{1-4}$ alkyl or $C(O)R_6$;

and pharmaceutically acceptable salts and solvates thereof.

A further embodiment of the invention provides compounds of formula (I) and pharmaceutically acceptable salts and solvates thereof, wherein
R represents halogen or $C_{1-4}$ alkyl;
$R_1$ represents $C_{1-4}$ alkyl;
$R_2$ represents hydrogen or $C_{1-4}$ alkyl;
$R_3$ represents hydrogen, or $C_{1-4}$ alkyl;
$R_4$ represents trifluoromethyl, $C_{1-4}$ alkyl, $C_{1-4}$ alkoxy, trifluoromethoxy or halogen;
$R_5$ represents hydrogen, $C_{1-4}$ alkyl, $C_{3-7}$ cycloalkyl or $S(O)_2R_6$;
$R_6$ represents $C_{1-4}$ alkyl or $C_{3-7}$ cycloalkyl;
m is zero or an integer from 1 to 3;
n is an integer from 1 to 3;
p is an integer from 1 to 2;
X and Y are independently C(O) or $CH_2$;

provided that
i) X and Y are not both C(O) and
ii) when X and Y are both $CH_2$, $R_5$ is not hydrogen or $C_{1-4}$ alkyl;

and pharmaceutically acceptable salts and solvates thereof.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, fumarates and maleates.

The solvates may, for example, be hydrates.

References hereinafter to a compound according to the invention include both compounds of formula (I) and their pharmaceutically acceptable acid addition salts together with pharmaceutically acceptable solvates.

Suitable pharmaceutical acceptable salts of the compounds of general formula (I) may be obtained in a crystalline form and/or in an amorphous form or as a mixture thereof.

It will be appreciated by those skilled in the art that the compounds of formula (I) contain at least two chiral centres (namely the carbon atoms shown as * in formula (I)) and these may be represented by the formulae (1a, 1b, 1c and 1d).

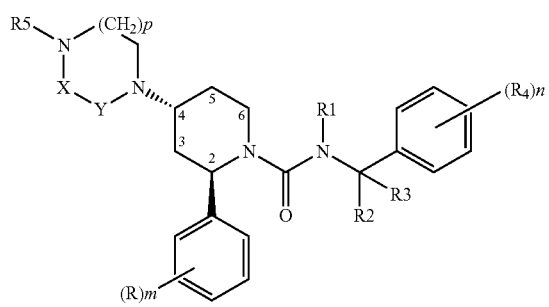

1a

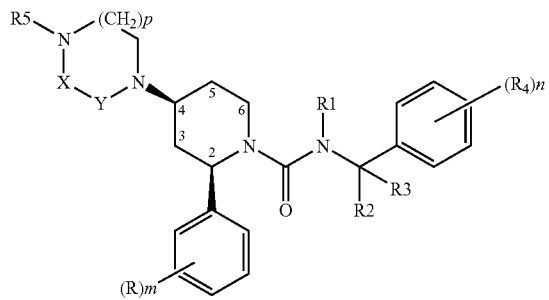

1b

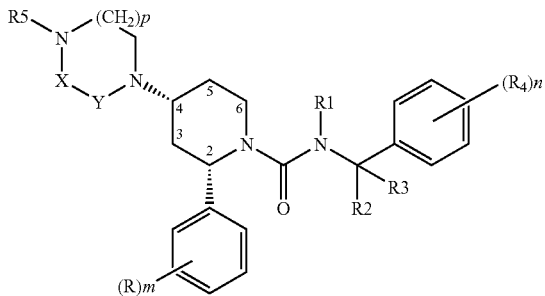

1c

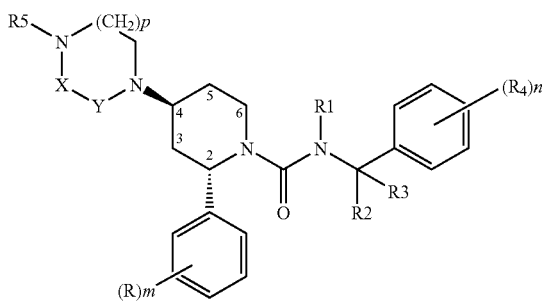

1d

The wedge shaped bond indicates that the bond is above the plane of the paper and is referred to as β configuration. The broken bond indicates that the bond is below the plane of the paper and is in the α configuration.

In general, in the specific compounds named below the β configuration at the 2 position of piperidine ring corresponds to the R configuration and the β configuration at the 4 position of piperidine ring corresponds to the S configuration. The a configuration at the 2 position of piperidine ring corresponds to the S configuration and the a configuration at the 4 position of piperidine ring corresponds to the R configuration. The assignment of the R or S configuration at the 2 and the 4 positions has been made according to the rules of Cahn, Ingold and Prelog, Experientia 1956, 12, 81.

Further asymmetric carbon atoms are possible in the compound of formula (I). Thus, when $R_2$ and $R_3$ are not the same group, the compounds of formula (I) possess at least four asymmetric carbon atoms.

It is to be understood that all stereoisomeric forms, including all enantiomers, diastereoisomers and all mixtures thereof, including racemates, are encompassed within the scope of the present invention and the reference to compounds of formula (I) includes all stereoisomeric forms unless otherwise stated.

Furthermore, some of the crystalline forms of the compounds of structure (I) may exist as polymorphs, which are included in the present invention.

The term $C_{1-4}$ alkyl as used herein as a group or a part of the group refers to a straight or branched alkyl group containing from 1 to 4 carbon atoms; examples of such groups include methyl, ethyl, propyl, isopropyl, n-butyl, isobutyl or tert butyl.

The term halogen refers to a fluorine, chlorine, bromine or iodine atom.

The term $C_{3-7}$ cycloalkyl group means a non aromatic monocyclic hydrocarbon ring of 3 to 7 carbon atoms such as, for example, cyclopropyl, cyclobutyl, cyclopentyl, cyclohexyl or cycloheptyl.

A preferred group of compounds of formula (I) are those in which the carbon atom at the 2-position of piperidine ring is in the β configuration.

When R represents halogen this is suitably chlorine or more preferably fluorine or when R is $C_{1-4}$ alkyl this is suitably methyl or ethyl wherein m is zero or an integer from 1 to 2.

Suitable values for $R_2$ or $R_3$ include hydrogen, a methyl, an ethyl or a propyl group.

R is preferably a halogen (e.g. fluorine) and/or a $C_{1-4}$ alkyl (e.g. methyl) group and m is preferably zero or an integer from 1 to 2.

$R_1$ is preferably a methyl group.

$R_2$ is preferably a hydrogen atom or a methyl group.

$R_3$ is preferably a hydrogen atom or a methyl group.

$R_4$ is preferably a trifluoromethyl group or halogen (i.e chlorine).

$R_5$ is preferably hydrogen, metyl, cyclopropyl, $C(O)CH_3$ or $S(O)_2CH_3$.

p is preferably 1.

A preferred class of compounds of formula (I) is that wherein each R is independently a halogen (e.g. fluorine) or a $C_{1-4}$ alkyl (e.g. methyl) group, wherein m is 0, 1 or 2. More preferably m is 1 or 2. Within this class those wherein R is at the 2 and/or 4 position in the phenyl ring are particularly preferred.

Compounds of formula (I), wherein n is 2, represent a preferred class of compounds and within this class the groups $R_4$ are preferably at the 3 and 5 position in the phenyl ring.

A further preferred class of compounds of formula (I) is that wherein

R is fluorine and/or methyl;
$R_1$ is preferably a methyl group;
$R_2$ is preferably a hydrogen atom or a methyl group;
$R_3$ is preferably a hydrogen atom or a methyl group;
$R_4$ is trifluoromethyl;
$R_5$ is preferably hydrogen, metyl, cyclopropyl, $C(O)CH_3$ or $S(O)_2CH_3$;
m is 1 or 2;
n is 2;
p is 1.

Preferred compounds according to the invention are:
2-(R)-(4-Fluoro-2-metyl-phenyl)-4-(R)-(3-oxo-piperazin-1-yl-)-piperidine-1-carboxylic acid, (3,5-bis-trifluoromethyl-benzyl)-methylamide;
2-(R)-(4-Fluoro-2-metyl-phenyl)-4-(S)-(3-oxo-piperazin-1-yl-)-piperidine-1-carboxylic acid, (3,5-bis-trifluoromethyl-benzyl)-methylamide;
2-(R)-(4-Fluoro-2-metyl-phenyl)-4-(R)-(4-methyl-3-oxo-piperazin-1-yl-)-piperidine-1-carboxylic acid, 1-(3,5-bis-trifluoromethyl-benzyl)-methylamide;
2-(R)-(4-Fluoro-2-metyl-phenyl)-4-(S)-(4-methyl-3-oxo-piperazin-1-yl-)-piperidine-1-carboxylic acid, 1-(3,5-bis-trifluoromethyl-benzyl)-methylamide;
2-(R)-(4-Fluoro-2-metyl-phenyl)-4-(S)-(4-methyl-3-oxo-piperazin-1-yl)-piperidine-1-carboxylic acid, [1 (R)-(3,5-bis-trifluoromethyl-phenyl)-ethyl]-methylamide;
2-(R)-(4-Fluoro-2-metyl-phenyl)-4-(R)-(2-oxo-piperazin-1-yl)-piperidine-1-carboxylic acid (3,5-bis-trifluoromethyl-benzyl)methylamide;
2-(4-Fluoro-2-methyl-phenyl)-4-(S)-(2-oxo-piperazin-1-yl)-piperidine-1-carboxylic acid, (3,5-bis-trifluoromethyl-benzyl)-methylamide;
2-(4-Fluoro-2-methyl-phenyl)-4-(S)-(2-oxo-piperazin-1-yl)-piperidine-1-carboxylic acid, (3,5-bis-trifluoromethyl-benzyl)-methylamide;
2-(R)-(4-Fluoro-2-methyl-phenyl)-4(S)-(2-oxo-4-methyl-piperazin-1-yl)-piperidine-1-carboxylic acid, (3,5-bis-trifluoromethyl-benzyl)-methylamide;
2-(R)$_4$-Fluoro-2-methyl-phenyl)-4-(S)-(4-methyl-2-oxo-piperazin-1-yl)piperidine-1-carboxylic acid, [1-(R)-(3,5-bis-trifluoromethyl-phenyl)-ethyl]-methylamide;
2-(R)-(4-Fluoro-2-methyl-phenyl)-4-(S)-(4-methyl-2-oxo-piperazin-1-yl)-piperidine-1-carboxilic acid, [1-(R)-(3,5-bis-trifluoromethyl-phenyl)-ethyl]-methylamide;
2-(R)-(4-Fluoro-2-methyl-phenyl)-4-(R)-(4-cyclopropyl-3-oxo-piperazin-1-yl-)-piperidine-1-carboxylic acid, 1-(3,5-bis-trifluoromethyl-benzyl)-methylamide;
2-(R)-(4-Fluoro-2-methyl-phenyl)-4-(S)-(4-cyclopropyl-3-oxo-piperazin-1-yl-)-piperidine-1-carboxylic acid, 1-(3,5-bis-trifluoromethyl-benzyl)-methylamide;
2-(R)-(4-Fluoro-2-methyl-phenyl)-4-(S)-(1-methanesulfonyl-piperazin-1-yl)-piperidine-1-carboxylic acid, 1-(3,5-bis-trifluoromethyl-benzyl)-methylamide;
2-(R)-(4-Fluoro-2-methyl-phenyl)-4-(S)-(1-methanesulfonyl-piperazin-1-yl)-piperidine-1-carboxylic acid, 1-[(R)-(3,5-bis-trifluoromethyl-phenyl)-ethyl]-methylamide;

and pharmaceutically acceptable salts and solvates thereof.

The compounds of the invention are antagonists of tachykinins, including substance P and other neurokinins, both in vitro and in vivo and are thus of use in the treatment of conditions mediated by tachykinins, including substance P and other neurokinins.

Tachykinins are a family of peptides that share a common carboxyl-terminal sequence (Phe-X-Gly-Leu-Met-NH2). They are actively involved in the physiology of both lower and advanced lifeforms. In mammalian lifeforms, the main tachykinins are substance P (SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1(SP-preferring), NK2 (NKA-preferring) and NK3 (NKB-preferring) which are widely distributed throughout the central nervous (CNS) and peripheral nervous system.

Particularly, the compounds of the invention are antagonists of the NK1 receptor.

By virtue of their efficacy as tachykinins receptor (expecially NK1 receptor) antagonists, the compounds of the present invention are particularly useful for the treatment of CNS disorders and psychotic disorders, in particular in the treatment or prevention of depressive states and/or in the treatment of anxiety.

$NK_1$-receptor binding affinity has been determined in vitro by measuring the compounds' ability to displace [3H]-substance P (SP) from recombinant human $NK_1$ receptor expressed in Chinese Hamster Ovary (CHO) cell membranes and from gerbil and marmoset brain cortex homogenates.

Membrane preparation from hNK1-CHO cells were performed essentially as described by Beattie et al. (Br. J. Pharmacol, 116:3149-3157, 1995).

hNK1-CHO cells were harvested in phosphate buffered saline (PBS) containing 5 mM EDTA and centrifuged at 913 g for 8 min at 4° C. Cells were then re-suspended in 10 volumes of membrane-preparation buffer (HBEPES 50 mM, pH 7.4, containing 0.1 mM leupeptin, 40 µg/ml bacitracin, 1 mM EDTA, 1 mM Pefabloc and 21M pepstatin A) and homogenised. The suspension was centrifuged at 48,000 g for 20 minutes at 4° C. The final pellet was re-suspended in 10 volumes of membrane preparation buffer and re-homogenised. Suspensions of membrane were then frozen at −80° C. until required.

The assay volume of 200 µl consisted of 211 of DMSO or increasing concentrations of test compound dissolved in DMSO (1 pM-1 µM final concentration), 100 µl of [3H]-SP (0.5 nM final concentration), and 100 µl of membrane suspension (8 µg of protein per well) in incubation buffer (containing 50 mM HEPES, pH 7.4, 3 mM MnCl2, and 0.02% BSA). The incubation was carried out at room temperature for 40 min. Non-specific binding was defined by the addition of cold SP (1 µM). The reaction was stopped by rapid filtration. Filters were washed 5 times with 200 µl of ice-cold 0.9% w/v NaCl, and radioactivity was counted in a microplate scintillation counter. In each experiment, every concentration of displacer was tested in duplicate.

Mongolian gerbil (60 g, Charles River) and common marmoset (Callithrix jacchus, 300-400 g, GSK colony, Verona, Italy) brain cortex homogenates were prepared as follows: fresh tissues were weighed, crumbled and homogenised in 10 volumes of membrane-preparation buffer. The homogenate was then centrifuged at 48,000 g for 20 minutes, and the pellet was washed once more by resuspension in 10 volumes of membrane preparation buffer and centrifugation at 48,000 g for 20 minutes. The final pellet was re-suspended in 7-10 volumes of membrane preparation buffer and subdivided in aliquots frozen at −80° C. until use.

The assay volume of 400 µl consisted of 100 µl of incubation buffer (containing 50 mM HEPES, pH 7.4, 3 mM MnCl2, and 0.02% BSA), 4 µl of DMSO or increasing concentrations of test compound dissolved in DMSO (1 pM-1 µM final concentration), 100 µl of [3H]-SP (0.5 nM-0.8 nM final concentration) in incubation buffer and 200 µl of membrane suspension (0.6 mg protein for gerbil, and 0.8 mg protein for marmoset) in incubation buffer containing 2 µg/ml leupeptin, 20 µg/ml bacitracin and 0.5 µM phosphoramidon. The incubation proceeded at room temperature for 60 min. Non-specific binding was defined by the addition of cold SP (1 µM). The reaction was stopped by rapid filtration. Filters were washed 3 times with 1 ml ice cold wash buffer (containing 50 mM HEPES, pH 7.4, and 3 mM MnCl2), and radioactivity was counted in a liquid scintillation counter.

The potency of test compounds to inhibit SP or GR73632-induced increase of [Ca2+]i in hNK1/CHO cells was determined in functional experiments by using FLIPR (fluorimetric imaging plate reader) technology.

hNK1/CHO cells were seeded at a density of 60,000 cells per well and cultured overnight in Ham's F-12 medium supplemented with 10% (v/v) heat-inactivated foetal bovine serum and 2 mM glutamine. The cells were then incubated for the labelling in the culture medium containing the fluorescent calcium indicator Fluo-4 AM (2 µM), the organic anions transport blocker probenecid (5 mM), and HEPES (20 mM) for 30 min in a humidified atmosphere of 5% CO2. After washing with Hanks' Balanced Salts Solution (HBSS) containing 20 mM HEPES and 2.5 mM probenecid, the cells were incubated for 60 min at 37 C in wash buffer containing 0.02% BSA either in the absence (control) or in the presence of test compounds. The plates were then placed into a FLIPR to monitor cell fluorescence (ex=488 nm, em=510-570 nm) before and after the addition of different concentrations of SP or GR73632 in assay buffer. Experiments were carried out by using a laser setting of 1.0 W and a 0.4 sec charge coupled device (CCD) camera shutter speed.

Compounds of the invention have also been found to exhibit anxiolytic activity in conventional tests. For example in marmoset human threat test (Costall et al., 1988).

The action of the compounds of the invention at the $NK_1$ receptor may be determined by using conventional tests. Thus, the ability to penetrate the central nervous system and to bind at the $NK_1$ receptor was demonstrated in vivo by their inhibitory effect on the change in the behaviour induced by intracerebroventricular applied substance P in the gerbil, according to the gerbil foot tapping model as described by Rupniak & Williams, Eur. J. of Pharmacol., 265, 179-183, 1994.

Compounds of the invention are useful in the treatment of CNS disorders and psychotic disorders, in particular in the treatment or prevention of depressive states and/or in the treatment of anxiety as defined in, but not restricted to, Diagnostic Statistical of Mental Disorder (DSM) IV edition edit by American Psychiatric Association and International Classification Diseases 10th revision (ICD10).

Thus, for example, depressive states include Major Depressive Disorders (MDD), including bipolar depression, unipolar depression, single or recurrent major depressive episodes, recurrent brief depression, with or without psychotic features, catatonic features, melancholic features including anorexia, weight loss, atypical features, anxious depression, cyclothymic or postpartum onset.

Other mood disorders encompassed within the term major depressive disorders include dysthymic disorders with early or late onset and with or without atypical features, neurotic depression, post-traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

The term anxiety includes anxiety disorders, such as panic disorders with or without agoraphobia, agoraphobia, phobias, for example, social phobias or agoraphobia, obsessive-compulsive disorder, stress disorders including post-traumatic stress disorders, generalised anxiety disorders, acute stress disorders and mixed anxiety-depression disorders.

Compounds of the invention are useful as analgesics. In particular, they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sports injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch and thalamic pain such as post stroke thalamic pain.

Compounds of the invention are also useful in the treatment of sleep disorders including dysomnia, insomnia, sleep apnea, narcolepsy, and circadian rythmic disorders.

Compounds of the invention are also useful in the treatment or prevention of the cognitive disorders. Cognitive disorders include dementia, amnestic disorders and cognitive disorders not otherwise specified.

Furthermore, compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds) or in the treatment of tolerance to and dependence on opiates (e.g. cannabis, heroin, morphine) or benzodiazepines; in the treatment of addiction to cocaine, sedative ipnotic, amphetamine or amphetamine-related drugs (e.g. dextroamphetamine, methylamphetamine) or a combination thereof.

Compounds of the invention are also useful as anti-inflammatory agents. In particular, they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment or prevention of schizophrenic disorders including paranoid schizophrenia, disorganised schizophrenia, catatonic schizophrenia, undifferentiated schizophrenia, residual schizophrenia.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia.

Compounds of the invention are also useful in the treatment of gastrointestinal disorders such as irritable bowel syndrome, gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia (such as ulcer-like dyspepsia, dysmotility-like dyspepsia and unspecified dyspepsia) chronic constipation; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The compounds of the invention are also useful in premenstrual dysphoric disorder (PMDD), in chronic fatigue syndrome and Multiple sclerosis.

Compounds of the invention have been found to exhibit anxiolytic and antidepressant activity in conventional tests. For example, in Guinea pig pups separation-induced vocalisations (Molewijk et al., 1996).

Compounds of the invention are also useful in the treatment of convulsions and epilepsy.

Compounds of the invention may be administered in combination with other active substances such as 5HT3 antagonists, serotonin agonists, selective serotonin re-uptake inhibitors (SSRI), noradrenaline re-uptake inhibitors (SNRI), tricyclic antidepressants or dopaminergic antidepressants.

Suitable 5HT3 antagonists which may be used in combination with the compounds of the inventions include for example ondansetron, granisetron and metoclopramide.

Suitable serotonin agonists which may be used in combination with the compounds of the invention include sumatriptan, rauwolscine, yohimbine and metoclopramide.

Suitable SSRI which may be used in combination with the compounds of the invention include fluoxetine, citalopram, femoxetine, fluvoxamine, paroxetine, indalpine, sertraline and zimeldine.

Suitable SNRI which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

It will be appreciated that the compounds of the combination may be administered simultaneously (either in the same or different pharmaceutical formulations) or sequentially.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus, compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Compounds of formula (I), and salts and solvates thereof, may be prepared by the general methods outlined hereinafter. In the following description, the groups R, $R_1$, $R_2$, $R_3$, $R_4$, $R_5$ $R_6$, m, n and p, have the meaning as previously defined for compounds of formula (I) unless otherwise stated.

Compounds of formula (I), wherein X is $CH_2$ or C(O) and Y is $CH_2$, may be prepared by reductive N-alkylation of a compound of formula (II),

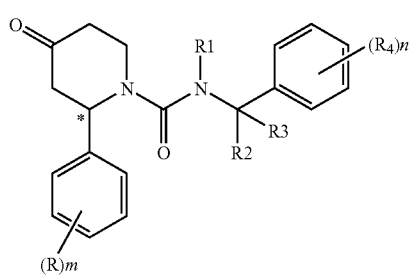

(II)

-continued

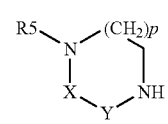

(III)

with a piperazine derivative (III) in an aprotic solvent such as dichloroethane and in the presence of a suitable metal reducing agent such as sodium borohydride or sodium triacetoxyborohydride.

Compounds of formula (II) may be prepared by treating compounds of formula (IV)

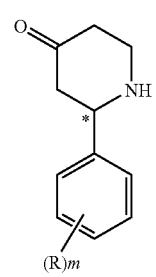

(IV)

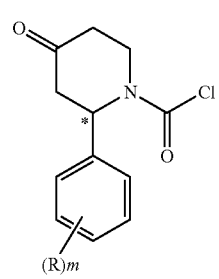

(V)

with triphosgene in an aprotic solvent such as dichloromethane and in the presence of an organic base such as triethylamine to form the intermediate carbonyl chloride compound (V) which may be isolated if required, followed by reaction of compound (V) with the amine compound (VI)

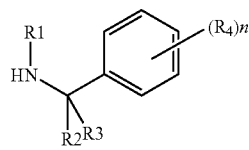

(VI)

The reaction conveniently takes place in an aprotic solvent such as a hydrocarbon, a halohydrocarbon such as dichloromethane or an ether such as tetrahydrofuran optionally in the presence of a base such as a tertiary amine e.g. diisopropylethylamine.

Compounds of formula (I), wherein Y is C(O), may be prepared by cyclisation of a compound of formula (VII), wherein P is a nitrogen protecting group, L is a suitable leaving group (i.e chlorine or bromine),

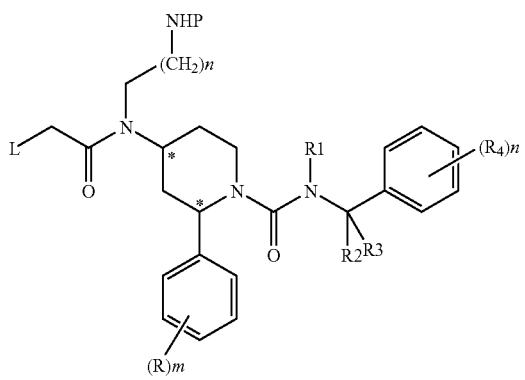

(VII)

followed by removal of any protecting group.

The cyclisation reaction takes place in an aprotic solvent such as dichloromethane at a temperature ranging from 0° to 25° C.

Suitable nitrogen protecting reagents are those described by T.W. Greene and P.G.M Wuts in Protective Groups in Organic Synthesis $2^{nd}$ ed., John Wiley & Son, Inc 1991, which is incorporated by reference. An example of a suitable nitrogen protecting group is t-butyloxycarbonyl.

Where it is desired to isolate a compound of formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts of the compounds of formula (I) using conventional methods.

Compounds of formula (IV), (V) and (VI) may be prepared by analogous methods to those used for known compounds.

Compound of formula (I) may be converted into another compound of formula (I). Thus, compounds of formula (I) wherein $R_5$ is $C(O)R_6$ or $S(O)_2R_6$ can be prepared by reaction of a compound of formula (I) wherein $R_5$ is hydrogen with L-C(O)$R_6$ or L-S(O)$_2R_6$, wherein L is a suitable leaving group (such as chlorine or bromine).

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, for example, specific enantiomers of the compounds of formula (I) may be obtained from the corresponding enantiomeric mixture of a compound of formula (I) using chiral HPLC procedure.

Alternatively, enantiomers of a compound of general formula (I) may be synthesised from the appropriate optically active intermediates using any of the general processes described herein.

Thus, for example the required enantiomer may be prepared by the corresponding chiral piperidin-4-one of formula (IV) using the process described above for preparing compounds of formula (I) from compounds (IV), followed by separation of the diastereomeric mixture of a compound of formula (I) using conventional procedure.

The chiral compounds (IV) may be prepared from the corresponding racemic compound (IV) using conventional procedures such as salt formation with a suitable optically active acid, separating the resultant diastereoisomeric salts by conventional means e.g. chromatography and crystallisation followed by hydrolysis of the diastereoisomeric salts.

A suitable optically active acid for use in the process is L(+)mandelic acid.

In a further embodiment of the invention the chiral compound (IV) may be prepared using Comins reaction as described in Journal American Chemical Society 1994,116, 47194728, followed by reduction of 2,3 dihydro-1H-pyridin-4-one derivative to piperidinone derivative. The reduction may be effected using hydrogen and metal catalyst e.g. palladium on a suitable support e.g. carbon or alumina. The reaction is carried out in a solvent such as ester e.g. ethyl acetate.

In a further embodiment of the invention the enantiomers of the compound of formula (I) may be prepared by reaction of a chiral amine (VI) using any of the processes described above for preparing compounds of formula (I) from amine (V).

The chiral amine (III) may be prepared from the corresponding racemic amine (III) using any conventional procedures such as salt formation with a suitable optically active acid.

The invention is further illustrated by the following Intermediates and Examples which are not intended as a limitation of the invention.

In the Intermediates and Examples unless otherwise stated:

Melting points (m.p.) were determined on a a Büchi 530 melting point apparatus and are uncorrected. All temperatures refers to IC. Infrared spectra were measured on a FT-IR instrument. $^1$H-NMR spectra were recorded on Varian instruments at 400 or 500 MHz, chemical shifts are reported in ppm (δ) using the residual solvent line as internal standard. The signals are assigned as singlets (s), doublets (d), doublets of doublets (dd), triplets (t), quartets (q) or multiplets (m). Mass spectra were taken on a VG Quattro mass spectrometer. Flash column chromatography was carried out over silica gel (Merck AG Darmstaadt, Germany). Optical rotations were determined at 20° C. with a Jasco DIP360 instrument (l=10 cm, cell volume=1 mL, A=589 nm). The following abbreviations are used in the text: AcOEt=ethyl acetate, CH=cyclohexane, DCM=dichloromethane, Et$_2$O=diethyl ether, DMF=N,N'-dimethylformamide, DIPEA=N,N-diisopropylethylamine, MeOH=methanol, TEA=triethylamine, TFA=trifluoroacetic acid, THF=tetaahydrofuran. T.l.c. refers to thin layer chromatography on 0.25 mm silica plates (60F-254 Merck) and dried refers to solution dried over anhydrous sodium sulphate; r.t. (RT) refers to room temperature.

Intermediate 1

1-(Benzyloxycarbonyl)-2-(4-fluoro-2-methyl-phenyl)-2,3-dihydro-4-pyridone

A small amount of iodine was added to a suspension of magnesium turnings (13.2 g) in dry THF (300 mL), at r.t., under a nitrogen atmosphere, then the mixture was vigorously refluxed for 20 minutes. To this suspension, a 15% of a solution of 2-bromo-5-fluoro-toluene (52.5 mL) in anhydrous THF (300 mL) was added. The suspension was heated under vigorous reflux until the brown colour disappeared. The remaining part of the bromide solution was added drop-wise over 1 hour to the refluxing suspension which was then stirred for a further 1 hour. This solution of Grignard reagent was then added drop-wise to the pyridinium salt obtained from benzyl chloroformate (48.7 mL) and 4-methoxypyridine (25 mL) in dry THF (900 mL) at −23° C.

The obtained solution was stirred 1 hour at −20° C. then it was warmed up to 20° C., a 10% hydrochloric acid solution (560 mL) was added and the aqueous layer was extracted with AcOEt (2×750 mL).

The combined organic extracts were washed with 5% sodium hydrogen carbonate solution (600 mL) and brine (600 mL) then partially concentrated in vacuo.

CH (400 mL) was added drop-wise over 1 hour at 20° C. and the resulting mixture was stirred 30 minutes and then filtered to give the title compound as a white solid (66 g).

IR (nujol, cm$^{-1}$): 1726 and 1655 (C=O), 1608 (C=C).

NMR (d$_6$-DMSO): δ (ppm) 8.19 (d, 1H); 7.31-7.18 (m, 5H); 7.08 (m, 2H); 6.94 (dt, 1H); 5.77 (d, 1H); 5.36 (d, 1H); 5.16 (2d, 2H); 3.26 (dd, 1H); 2.32 (d, 1H); 2.26 (s, 3H).

MS (ES/+): m/z=340 [MH]$^+$.

Intermediate 2

2-(4-Fluoro-2-methyl-phenyl)-piperidine-4-one

Method A

4-Fluoro-2-methyl-benzaldehyde (4 g) was added to a solution of 4-aminobutan-2-one ethylene acetal (3.8 g) in dry benzene (50 mL) and the solution was stirred at r.t. under a nitrogen atmosphere. After 1 hour the mixture was heated at reflux for 16 hours and then allowed to cool to r.t. This solution was slowly added to a refluxing solution of p-toluensulphonic acid (10.6 g) in dry benzene (50 mL) previously refluxed for 1 hour with a Dean-Stark apparatus. After 3.5 hours the crude solution was cooled and made basic with a saturated potassium carbonate solution and taken up with AcOEt (50 mL). The aqueous phase was extracted with AcOEt (3×50 mL) and Et2O (2×50 mL). The organic layer was dried and concentrated in vacuo to a yellow thick oil as residue (7.23 g). A portion of the crude mixture (3 g) was dissolved in a 6N hydrochloric acid solution (20 mL) and stirred at 60° C. for 16 hours. The solution was basified with solid potassium carbonate and extracted with DCM (5×50 mL). The combined organic phases were washed with brine (50 mL), dried and concentrated in vacuo to give the title compound (2.5 g) as a thick yellow oil.

Method B

L-selectride (1M solution in dry THF, 210 mL) was added drop-wise, over 80 minutes, to a solution of intermediate 1 (50 g) in dry THF (1065 mL) previously cooled to −72° C. under a nitrogen atmosphere. After 45 minutes, 2% sodium hydrogen carbonate solution (994 mL) was added drop-wise and the solution was extracted with AcOEt (3×994 mL). The combined organic phases were washed with water (284 mL) and brine (568 mL). The organic phase was dried and concentrated in vacuo to get 1-benzyloxycarbonyl-2-(4-fluoro-2-methyl-phenyl)-piperidine-4-one as a pale yellow thick oil (94 g) which was used as a crude.

This material (94 g) was dissolved in AcOEt (710 mL), then 10% Pd/C (30.5 g) was added under a nitrogen atmosphere. The slurry was hydrogenated at 1 atmosphere for 30 minutes. The mixture was filtered through Celite and the organic phase was concentrated in vacuo to give the crude 2-(4-fluoro-2-methyl-phenyl)piperidine-4-one as a yellow oil. This material was dissolved in AcOEt (518 mL) at r.t. and racemic camphorsulphonic acid (48.3 g) was added. The mixture was stirred at r.t for 18 hours, then the solid was filtered off, washed with AcOEt (2×50 mL) and dried in vacuo for 18 hours to give 2-(4-fluoro-2-methyl-phenyl)-piperidine-4-one, 10-camphorsulfonic acid salt as a pale yellow solid (68.5 g). (M.p.: 167-169° C.—NMR (d$_6$-DMSO): δ (ppm) 9.43 (bs, 1H); 9.23 (bs, 1H); 7.66 (dd, 1H); 7.19 (m, 2H); 4.97 (bd, 1H); 3.6 (m, 2H); 2.87 (m, 3H); 2.66 (m, 1H); 2.53 (m, 2H); 2.37 (s+d, 4H); 2.22 (m, 1H); 1.93 (t, 1H); 1.8 (m, 2H); 1.26 (m, 2H); 1.03 (s, 3H); 0.73 (s, 3H).

This material (68.5 g) was suspended in AcOEt (480 mL) and stirred with a saturated sodium hydrogen carbonate (274 mL). The organic layer was separated and washed with further water (274 mL). The organic phase was dried and concentrated in vacuo to give the title compound (31 g) as a yellow-orange oil.

NMR (d$_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H).

MS (ES/+): m/z=208 [MH]$^+$.

Intermediate 3

2-(4-Fluoro-2-methyl-phenyl)-4-oxo-piperidine-1-carboxylic Acid (3.5-bis-trifluoromethyl-benzyl)-methylamide A solution of triphosgene (1.43 g) dissolved in dry DCM (10 mL) was added to a solution of intermediate 2 (2.5 g) and DIPEA (8.4 mL) in dry DCM (20 mL) previously cooled to 0° C. under a nitrogen atmosphere. The solution was stirred at 0° C. for 2 hours, then (3,5-bis-trifluoromethyl-benzyl)-methylamine hydrochloride (5.63 g) and DIPEA (3.34 mL) were added. The mixture was stirred under nitrogen at r.t. for 14 hours. The mixture was taken up with AcOEt (50 mL), washed with cold 1N hydrochloric acid solution (3×20 mL) and brine (10 mL). The organic layer was dried and concentrated in vacuo to a residue which was purified by flash chromatography (AcOEt/CH 3:7) to give the title compound as a white foam (3.85 g).

IR (nujol, cm$^{-1}$): 1721 and 1641 (C=O).

NMR (d$_6$-DMSO): δ (ppm) 7.96 (s, 1H); 7.76 (s, 2H); 7.25 (dd, 1H); 6.97 (dd, 1H); 6.90 (dt, 1H); 5.22 (t, 1H); 4.59 (d, 1H); 4.43 (d, 1H); 3.63-3.49 (m, 2H); 2.79 (s, 3H); 2.69 (m, 2H); 2.49 (m, 2H); 2.26 (s, 3H).

MS (ES/+): m/z=491 [MH]$^+$.

Intermediate 4

2-(R)-(4-Fluoro-2-methyl-phenyl)-4-oxo-piperidine-1-carboxylic acid [1-(R)-3,5-bis-trifluoromethyl-phenyl)-ethyl]-methylamide (4a) and 2-(S)-(4-Fluoro-2-methyl-phenyl)-4-oxo-piperidine-1-carboxylic acid [1-(R)-3,5-bis-trifluoromethyl-phenyl)-ethyl]-methylamide (4b)

Method A

A solution of triphosgene (147 mg) dissolved in dry DCM (5 mL) was added drop-wise to a solution of intermediate 2 (250 mg) and DIPEA (860 μL) in dry DCM (15 mL) previously cooled to 0° C. under a nitrogen atmosphere. After 2 hours, [1-(R)-3,5-bis-trifluoromethyl-phenyl)ethyl]-methylamine hydrochloride (503 mg) and DIPEA (320 μL) in dry acetonitrile (20 mL) were added and the mixture was heated to 70° C. for 16 hours. Further [1-(R)-(3,5-bis-trifluoromethyl-phenyl)ethyl]-methylamine hydrochloride (170 mg) and DIPEA (100 μL) were added and the mixture was stirred at 70° C. for further 4 hours. Next, the mixture was allowed to cool to r.t., taken up with AcOEt (30 mL), washed with a 1N hydrochloric acid cold solution (3×15 mL) and brine (2×10 mL). The organic layer was dried and concentrated in vacuo to a residue, which was purified by flash chromatography (CH/AcOEt 8:2) to give:
1. intermediate 4a (230 mg) as a white foam,
2. intermediate 4b (231 mg) as a white foam.

Intermediate 4a

NMR ($d_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 31); 2.50 (m, 2H); 2.26 (s, 3H); 1.57 (d, 3H).

Intermediate 4b

NMR ($d_6$-DMSO): δ (ppm) 7.96 (bs, 1H); 7.75 (bs, 2H); 7.24 (dd, 1H); 6.98 (dd, 1H); 6.93 (dt, 1H); 5.29 (q, 1H); 5.24 (t, 1H); 3.56 (m, 1H); 3.48 (m, 1H); 2.70 (s, 3H); 2.50 (m, 4H); 2.26 (s, 3H); 1.54 (d, 3H).

Intermediate 4a

Method B

A saturated sodium hydrogen carbonate solution (324 mL) was added to a solution of intermediate 9 (21.6 g) in AcOEt (324 mL) and the resulting mixture was vigorously stirred for 15 minutes. The aqueous layer was back-extracted with further AcOEt (216 mL) and the combined organic extracts were dried and concentrated in vacuo to give intermediate 8 as a yellow oil, which was treated with TEA (19 mL) and AcOEt (114 mL). The solution obtained was added drop-wise over 40 minutes to a solution of triphosgene (8 g) in AcOEt (64 mL) previously cooled to 0° C. under a nitrogen atmosphere, maintaining the temperature between 0° C. and 8° C.

After stirring for 1 hours at 0° C. and for 3 hours at 20° C., [1-(R)-(3,5-bis-trifluoromethl-phenyl)-ethyl]-methylamine hydrochloride (29.7 g), AcOEt (190 mL) and TEA (38 mL) were added to the reaction mixture which was then heated to reflux for 16 hours.

The solution was washed with 10% sodium hydroxide solution (180 mL), 1% hydrochloric acid solution (4×150 mL), water (3×180 mL) and brine (180 mL). The organic layer was dried and concentrated in vacuo to a residue, which was purified through a silica pad (CH/AcOEt 9:1) to give the title compound (21.5 g) as a brown thick oil.

NMR ($d_6$-DMSO): δ (ppm) 7.97-7.77 (bs+bs, 3H); 7.24 (dd, 1H); 6.97 (dd, 1H); 6.88 (td, 1H); 5.24 (m, 1H); 5.14 (q, 1H); 3.58 (m, 2H); 2.7 (m, 2H); 2.56 (s, 3H); 2.49 (m, 2H); 2.26 (s, 3H); 1.57 (d, 3H).

Intermediate 5

2-(S)-(4-Fluoro-2-methyl-phenyl)-4-oxo-piperidine-1-carboxylic Acid [1-(S)-(3,5-bis-trifluoromethyl-phenyl)-ethyl]-methylamide (5a) and 2-(R)(4-Fluoro-2-methyl-phenyl)oxo-piperidine-1-carboxylic Acid [1-(S)-(3,5-bis-trifluoromethyl-phenyl)-ethyl]-methylamide (5b)

A solution of triphosgene (147 mg) dissolved in dry DCM (5 mL) was added to a solution of intermediate 2 (250 mg) and DIPEA (860 µL) in dry DCM (15 mL) previously cooled to 0° C. under a nitrogen atmosphere. After 2 hours, a solution of [1-(S)-(3,5-bis-trifluoromethyl-phenyl)-ethyl]-methylamine hydrochloride (510 mg) and DIPEA (320 µL) in dry acetonitrile (20 mL) was added and the mixture was heated to 70° C. for 16 hours. Next, further [1-(S)-(3,5-bis-trifluoromethyl-phenyl)-ethyl]-methylamine hydrochloride (170 mg) and DIPEA (105 µL) were added. After further 4 hours at 70° C., the mixture was allowed to cool to r.t., taken up with AcOEt (30 mL), washed with a 1N hydrochloric acid cold solution (3×15 mL) and brine (2×10 mL). The organic layer was dried and concentrated iii vacuo to a residue, which was purified by flash chromatography (CH/AcOEt 8:2) to give:
1. intermediate 5a (234 mg) as a white foam,
2. intermediate 5b (244 mg) as a white foam.

Intermediate 5a

NMR ($d_6$-DMSO): δ (ppm) 7.97-7.77 (bs+bs, 3H); 7.24 (dd, 1 µl); 6.97 (dd, 1H); 6.88 (td, 1H); 5.24 (m, 1H); 5.14 (q, 1H); 3.58 (m, 2H); 2.7 (m, 2H); 2.56 (s, 3H); 2.49 (m, 2H); 2.26 (s, 3H); 1.57 (d, 3H).

Intermediate 5b

NMR ($d_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).

Intermediate 6

2-(S)-(4-Fluoro-2-methyl-phenyl)-4-oxo-3,4-dihydro-2H-pyridine-1-carboxylic Acid (1R, 2S, 5R)-2-isopropyl-5-methyl-cyclohexyl Ester (6a) and 2-(R)-(4-Fluoro-2-methyl-phenyl-4-oxo-3,4-dihydro-2H-pyridine-1-carboxylic Acid (1R, 2S, 5R)-2-isopropyl-5-methyl-cyclohexyl Ester (6b)

A solution of 2-bromo-5-fluoro-toluene (3.68 g) in dry THF (10 mL) was dropped over 30 minutes, into a mixture of magnesium (525 mg) and iodine (1 crystal) in dry THF (5 mL) previously heated to 70° C. under a nitrogen atmosphere. The mixture was stirred at 70° C. for 1.5 hours, then allowed to cool to r.t.

A solution of (−)-mentyl chloroformate (3.53 mL) in dry THF (15 mL) was added to a solution of 4-methoxypyridine (1.52 mL) in dry THF (35 mL) previously cooled to −78° C. under a nitrogen atmosphere. After 15 minutes, the solution containing the 4-fluoro-2-methyl-phenyl magnesium bromide was added drop-wise, and the mixture was stirred at −78° C. for 1 hour. The reaction was quenched by the addition of 1M hydrochloric acid solution (20 mL), warmed to r.t. and stirred at 23° C. for 30 minutes. After extraction with AcOEt (2×150 mL), the combined organic extracts were washed with brine (50 mL), dried and concentrated in vacuo to a residue, which was purified by flash chromatography (CH/THF/toluene 8:1:1) to give:
1. intermediate 6a (3.44 g—yellow oil)
2. intermediate 6b (530 mg—white solid).

Intermediate 6a

T.l.c.: CH/THF/toluene 7:2:1, Rf=0.59.
IR (nujol, $cm^{-1}$): 1718 and 1675 (C=O).
NMR ($d_6$-DMSO): δ (ppm) 8.14 (d, 1H); 7.08 (dd, 1H); 7.02 (dd, 1H); 6.95 (m, 1H); 5.68 (d, 1H); 5.34 (d, 1H); 4.47 (m, 1H); 3.26 (dd, 1H); 2.30 (m, 4H); 1.7 (m, 4H); 1.33 (m, 2H); 0.8 (m, 11H).

Intermediate 6b

M.p.: 117-120° C.
T.l.c.: CH/THF/toluene 7:2:1, Rf=0.56.
IR (nujol, $cm^{-1}$): 1718 and 1669 (C=O).
NMR ($d_6$-DMSO): δ (ppm) 8.17 (d, 1H); 7.04-6.94 (m, 3H); 5.70 (d, 1H); 5.35 (d, 1H); 4.42 (m, 1H); 3.26 (dd, 1H); 2.30 (m, 4H); 1.58-1.40 (m, 3H); 1.2-0.7 (m, 8H; 0.51-0.34 (bs, 6H):

Intermediate 7

2-(R)-(4-Fluoro-2-methyl-phenyl)-2,3-dihydro-1H-pyridin-4-one

Sodium methoxide (100 mg) was added to a solution of intermediate 6b (170 mg) in MeOH (15 mL) under a nitrogen atmosphere. The mixture was refluxed for two hours and the solvent was removed in vacuo. The residue was partitioned between water (10 mL) and AcOEt (15 mL). The layers were separated, and the aqueous phase was extracted with further AcOEt (4×10 mL). The combined organic extracts were washed with brine (10 mL), dried and concentrated in vacuo to give the title compound (145 mg) as a light yellow oil.

NMR ($d_6$-DMSO): δ (ppm) 7.71 (bd, 1H); 7.45 (dd, 1H); 7.38 (t, 1H); 7.03 (m, 2H); 4.86 (dd, 1H); 4.77 (d, 1H); 2.42 (dd, 1H); 2.3.1 (m, 4H).

MS (ES/+): m/z=206 $[M+H]^+$.

Intermediate 8

2-(R)-(4-Fluoro-2-methyl-phenyl)-piperidin-4-one

Palladium over charcoal (10%-74 mg) was added to a solution of intermediate 7 (145 mg) in MeOH (8 mL) and THF (2 mL). The mixture was allowed to react with hydrogen in a pressure reactor (2 atm) overnight. After flushing with nitrogen, the solution was filtered and the solvent removed in vacuo. The crude product was purified by flash chromatography (AcOEt/MeOH 9:1) to give the title compound (26 mg) as a yellow oil.

The enantiomeric excess (90-95%) was detected by chiral HPLC.

T.l.c.: AcOEt/MeOH 9:1, Rf=0.2.

NMR ($d_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 31); 2.25 (dt, 1H); 2.18 (m, 1H).

MS (ES/+): m/z=208 $[MH]^+$.

$[α]_D$=+82.1 (c=1.07, DMSO).

Intermediate 9

2-(R)-(4-Fluoro-2-methyl-phenyl)-piperidin-4-one Mandelic Acid

A solution of L-(+)-mandelic acid (22.6 g) in AcOEt (308 mL) was added to a solution of intermediate 2 (31 g) in AcOEt (308 mL). Then isopropanol (616 mL) was added and the solution was concentrated in vacuo to 274 mL. The solution was then cooled to 0° C. and further cold isopropanol (96 mL) was added. The thick precipitate was stirred under nitrogen for 5 hours at 0° C., then filtered and washed with cold Et2O (250 mL) to give the title compound as a pale yellow solid (20.3 g).

M.p.: 82-85° C.

NMR ($d_6$-DMSO): δ (ppm) 7.51 (dd, 1H); 7.40 (m, 21); 7.32 (m, 2H); 7.26 (m, 1H); 7.0 (m, 2H); 4.95 (s, 1H); 4.04 (dd, 1H); 3.31 (m, 1H); 2.88 (m, 1H); 2.49-2.2 (m, 4H); 2.29 (s, 3H). Chiral HPLC: HP 1100 HPLC system; column Chiralcel OD-H, 25 cm×4.6 mm; mobile phase: n-hexane/isopropanol 95:5+1% diethylamine; flow: 1.3 ml/min; detection: 240/215 nm; retention time 12.07 minutes.

Intermediate 10

2-(R)-4-Fluoro-2-methyl-phenyl)-4-oxo-piperidine-1-carboxylic Acid (3.5-bis-trifluoromethyl-benzyl)-methylamide Method A A solution of triphosgene (17 mg) in dry DCM (2 mL) was added to a solution of intermediate 8 (26 mg) and DIPEA (65 mg) in dry DCM (3 mL) previously cooled to 0° C. under a nitrogen atmosphere. After two hours acetonitrile (10 mL) was added, the temperature was allowed to reach r.t and the DCM evaporated under a nitrogen flush. Then, a solution of 3,5-bis-trifluoromethyl-benzyl)-methylamine hydrochloride (74 mg) and DIPEA (130 mg) in acetonitrile (3 mL) was added and the mixture was stirred at 23° C.

overnight. The solvent was concentrated in vacuo. The residue was dissolved in AcOEt (10 mL) and washed with 1N hydrochloric acid solution (3×5 mL), 5% sodium hydrogen carbonate (5 mL) and brine (10 mL). The organic layer was dried and concentrated in vacuo to a residue, which was purified by flash chromatography (CH/AcOEt 1:1) to give the title compound (50 mg) as a white solid.

Method B

A saturated sodium hydrogen carbonate solution (348 mL) was added to a solution of intermediate 9 (23.2 g) in AcOEt (348 mL) and the resulting mixture was vigorously stirred for 15 minutes. The aqueous layer was back-extracted with further AcOEt (230 mL) and the combined organic extracts were dried and concentrated in vacuo to give intermediate 8 (12.31 g) as a yellow oil, which was treated with TEA (20.5 mL) and AcOEt (123 mL). The solution obtained was added drop-wise over 40 minutes to a solution of triphosgene (8 g) in AcOEt (61 mL) previously cooled to 0° C. under a nitrogen atmosphere, maintaining the temperature between 0° C. and 8° C.

After stirring for 2 hours at 20° C., 3,5-(bis-trifluoromethyl-benzyl)-methylamine hydrochloride (28.1 g), AcOEt (184 mL) and TEA (33 mL) were added to the reaction mixture which was then further stirred for 2 hours at 20° C.

The solution was washed with 10% sodium hydroxide solution (3×185 mL) and 1% hydrochloric acid solution (3×185 mL). The organic layer was dried and concentrated in vacuo to a crude (38 g), which was purified through a silica pad (CI/AcOEt from 9:1 to 1:1) to give the title compound (24.7 g) as a colourless oil.

NMR ($d_6$-DMSO): δ (ppm) 7.96 (s, 1H); 7.76 (s, 2H); 7.26 (dd, 1H); 6.98 (dd, 1H); 6.90 (td, 1H); 5.23 (t, 1H); 4.61 (d, 1H); 4.41 (d, 1H); 3.60 (m, 2H); 2.69 (m, 2H); 2.79 (s, 3H); 2.50 (m, 2H); 2.27 (s, 3H).

MS (ES/+): m/z=491 $[MH]^+$.

Intermediate 11

3-Oxo-piperazine-1-carboxylic Acid tert-butyl Ester

Di-tert-butyl-dicarbonate (647 mg) and TEA (0.937 mL) were added to a solution of 2-oxo-piperazine (267 mg) in DCM (30 mL) under a nitrogen atmosphere. The mixture was stirred for 4 hours at r.t., then concentrated in vacuo to a residue which was purified by flash chromatography (AcOEt/MeOH 8:2) to give the title compound (355 mg) as a white solid.

T.l.c.: AcOEt/MeOH 8:2, Rf=0.14.

IR (nujol, $cm^{-1}$): 3412 (NH), 1677 (C=O).

NMR ($d_6$-DMSO): δ (ppm) 6.40 (bs, 1H); 4.10 (dd, 2H); 3.64 (t, 21); 3.39 (m, 2H); 1.48 (s, 9H).

MS (ES/+): m/z=201 $[M+H-HCl]^+$, 223 $[M-HCl+Na]^+$, 145 $[M+H-tBu+H]^+$.

Intermediate 12

4-Methyl-3-oxo-piperazine-1-carboxylic Acid Tert-butyl Ester

Sodium hydride (60% suspension in oil, 105 mg) was added to a solution intermediate 11 (351 mg) in anhydrous THF (30 mL) and DMF (6 mL) under a nitrogen atmosphere. The mixture was stirred at r.t. for 1 hour, then iodomethane (0.218 mL) was added. The solution was warmed at 80° C. for 3 hours, then was cooled to r.t. and a saturated ammonium chloride solution was added. The organic layer was washed with iced water (20 mL) and brine (20 mL). The solution was concentrated in vacuo to give the title compound (195 mg) as a yellow oil.

T.l.c.: AcOEt/MeOH/TEA 80:20:1, Rf=0.51.

NMR (CDCl3): δ (ppm) 4.05 (s, 2H); 3.65 (m, 2H); 3.30 (m, 2H); 1.45 (m, 9H).

Intermediate 13

{2-[1-(3,5-Bis-trifluoromethyl-benzyl)-methyl-carbamoyl]-2-(R)-(4-fluoro-2-methyl-phenyl)-piperidin-4(R)-yl-amino]-ethyl}-carbamic Acid Tert-butyl Ester (13a) and {2-[1-(3,5-Bis trifluoromethyl-benzyl)-methyl-carbamoyl]-2-(R)-(4-fluoro-2-methyl-phenyl)-piperidin-4-(S)-yl-amino]-ethyl}-carbamic Acid, Tert-butyl Ester (13b)

N-BOC-ethylenediamine (0.109 mL) was added to a solution of intermediate 10 (152 mg) in dry 1,2-dichloroethane (3 mL) and dry acetonitrile (3 mL) under a nitrogen atmosphere. The mixture was stirred at 23° C. for 16 hour, then sodium triacetoxyborohydride (98 mg) was added and the solution was stirred at 23° C. for 6 hours. The solution was washed with a 5% sodium hydrogen carbonate solution (10 mL) and brine (10 mL). The organic layer was dried and concentrated in vacuo to a residue which was purified by flash chromatography (AcOEt/MeOH 8:2) to give two fractions:

1. intermediate 13a (65 mg)
2. intermediate 13b (39 mg)

Intermediate 13a:

T.l.c.: AcOEt/MeOH 8:2, Rf=0.41.

NMR ($d_6$-DMSO): δ (ppm) 7.91 (bs, 1H); 7.62 (bs, 2H); 7.21 (dd, 1H); 6.87 (dd, 1H); 6.67 (m, 1H); 6.71 (bt, 1H); 4.63 (m, 1H); 4.53 (d, 1H); 4.35 (d, 1H); 3.3-2.8 (m, 5H); 2.83 (s, 3H); 2.51 (bm, 2H); 2.25 (s, 3H); 1.90-1.45 (m, 4H); 1.33 (s, 9H).

MS (ES/+): m/z=635 [MH]$^+$, 579 [M−tBu+H]$^+$.

Intermediate 13b:

T.l.c.: AcOEt/MeOH 8:2, Rf=0.25.

NMR ($d_6$-DMSO): δ (ppm) 7.90 (bs 1H); 7.55 (bs 2H); 7.16 (dd, 1H); 6.85 (dd, 1H); 6.73 (m, 1H); 6.64 (bt, 1H); 4.58 (d, 1H); 4.31 (d, 1H); 4.09 (dd, 1H); 3.37 (m, 1H); 2.91 (m, 2H); 2.87 (s, 3H); 2.64 (m, 1H); 2.52 (m, 3H); 2.30 (s, 3H); 1.89 (m, 2H); 1.82 (m, 2H), 1.31 (s, 9H). MS (ES/+): m/z=635 [MH]$^+$, 579 [M−tBu+H]$^+$.

Intermediate 14

{2-[1-{[1-(R)-(3,5-Bis-trifluoromethyl-phenyl)-ethyl]-methyl-carbamoyl}-2-(R)-(4-fluoro-2-methyl-phenyl)-piperidin-4-(R)-yl-amino]-ethyl}-carbamic Acid Tert-butyl Ester (14a) and {2-[1-{[1-(R)-(3,5-Bis-trifluoromethyl-phenyl)-ethyl]-methyl-carbamoyl}-2-(R)-(4-fluoro-2-methyl-phenyl)piperidin-4-(S)-yl-amino]-ethyl}-carbamic Acid Tert-butyl Ester (14b)

N-BOC-ethylenediamine (0.435 ml) was added to a solution of intermediate 4a (462 mg) in dry 1,2-dichloroethane (9 mL) and dry acetonitrile (9 mL) under a nitrogen atmosphere. The mixture was stirred at 23° C. for 30 minutes, then sodium triacetoxyborohydride (298 mg) was added. The solution was stirred at 23° C. for 16 hours, then washed with a 5% sodium hydrogen carbonate solution (10 mL) and brine (10 mL). The organic layer was dried and concentrated in vacuo to a residue which was purified by flash chromatography (AcOEt/MeOH 9:1) to give two fractions.

1. intermediate 14a (252 mg—T.l.c.: AcOEt/MeOH 8:2 Rf=0.42).
2. intermediate 14b (116 mg—T.l.c.: AcOEt/MeOH 8:2 Rf=0.34).

Intermediate 14a:

NMR ($d_6$-DMSO): δ (ppm) 7.98 (bs, 1H); 7.71 (bs, 2H); 7.23 (dd, 1H); 6.92 (dd, 1H); 6.80 (dt, 1H); 6.74 (bt, 1H); 5.22 (q, 1H); 4.73 (dd, 1H); 3.27 (m, 1H); 3.09 (m, 1H); 3.01 (m, 2H); 2.87 (m, 2H); 2.66 (s, 3H); 2.52 (m, 2H); 2.28 (s, 3H); 1.87 (m, 1H); 1.80 (bs, 11H); 1.65 (m, 2H); 1.49 (m, 4H); 1.37 (s, 9H).

MS (ES/+): m/z=649 [M+H]$^+$; 593 [M−tBu+H]$^+$, 549 [M+H−BOC+H].

Intermediate 14b:

NMR ($d_6$-DMSO): δ (ppm) 7.99 (s, 1H); 7.68 (s, 2H); 7.14 (dd, 1H); 6.90 (dd, 1H); 6.76 (dt, 1H); 6.70 (bs, 1H); 5.31 (m, 1H); 4.13 (dd, 1H); 3.3 (m, 2H); 2.97 (m, 3H); 2.72 (s, 3H); 2.59 (bs, 2H); 2.34 (s, 3H); 1.8-1.4 (bm, 5H); 1.46 (d, 3H); 1.36 (s, 9H).

MS (ES/+): m/z=649 [M+H]$^+$, 593 [M−tBu+H]$^+$.

Intermediate 15

(2-Cyclopropylamino-ethyl)-carbamic Acid Tert-butyl Ester

Cyclopropylamine (866 µl) was added to a solution of tert-butyl-N-(2-oxo-ethyl)carbammate (1 g) in MeOH (50 mL) under a nitrogen atmosphere. The resulting solution was stirred at 23° C. for 1 hour, then potassium borohydride (372 mg) was added and the mixture was stirred at 23° C. for a further 1 hour. The mixture was concentrated to half volume, diluted with a saturated sodium hydrogen carbonate solution (20 mL) and extracted with AcOEt (2×30 mL). The combined organic extracts were dried, concentrated in vacuo to a residue, which was purified by flash chromatography (AcOEt/MeOH 9:1) to give the title compound (1.22 g) as a yellow oil.

NMR (CDCl3): δ (ppm) 8.25 (bm, 1H); 3.2 (dd, 2H); 2.8 (dd, 2H); 2.1 (m, 1H); 1.42 (s, 9H); 0.42 (dd, 2H); 0.29 (m, 2H).

MS (ES/+): m/z=201 [M+H]$^+$, 145 [M−tBu]$^+$.

Intermediate 16

{2-[(2-Bromoacetyl)-cyclopropyl-amino]-ethyl}carbamic Acid Tert-butyl Ester

TEA (719 µL) and bromoacetylbromide (0.27 µL) were added to a solution of intermediate 15 (511 mg) in anhydrous DCM (25 mL) previously cooled to 0° C. under a Nitrogen atmosphere. The solution was stirred at 0° C. for 30 minutes, then it was quenched with brine (15 mL). The layers were separated and the organic phase was dried and concentrated in vacuo. The residue was purified by flash chromatography (CH/AcOEt 65:35) to give the title compound (394 mg) as a yellow solid.

T.l.c.: CH(AcOEt 1:1, Rf=0.43 (detection only with ninhydrin).

NMR (CDCl3): δ (ppm) 4.85 (bm, 1H); 4.1 (s, 2H); 3.5 (m, 2H); 3.3 (m, 2H); 2.88 (m, 1H); 1.42 (s, 9H); 0.95 (m, 2H); 0.85 (m, 2H).

Intermediate 17

4-Cyclopropyl-3-oxo-piperazine-1-carboxylic Acid Tert-butyl Ester

Sodium hydride (60% dispersion in mineral oil—147 mg) was added to a solution of intermediate 16 (394 mg) in anhydrous THF (12 mL) and DMF (12 mL) previously cooled to 0° C. under a Nitrogen atmosphere. The mixture was stirred at 0° C. for 1.5 hours, then water (20 mL) was added and the mixture was extracted with AcOEt (3×30 mL). The combined organic extracts were washed with cold water (20 mL) and brine (20 mL), dried and concentrated in vacuo. The residue was purified by flash chromatography (CH/AcOEt 1:1) to give the title compound (210 mg) as a yellow oil.

T.l.c.: CH/AcOEt 1:1, Rf=0.23 (detection only with ninhydrin).

NMR (CDCl3): δ (ppm) 5.5 (m, 2H); 4.0 (s, 2H); 3.23 (m, 2H); 2.7 (m, 1H); 1.42 (s, 9H); 0.8 (m, 2H); 0.65 (m, 2H).

Intermediate 18

4-(R)-[1-[(3,5-Bis-trifluoromethyl-benzyl)-methyl-carbamoyl]-2-(R)-(4-fluoro-2-methyl-phenyl)-piperidin-4-yl]-piperazine-1-carboxylic Acid Tert-butyl Ester (18a) and 4-(S)-[1-[(3,5-Bis-trifluoromethyl-benzyl)methyl-carbamoyl]-2-(R)-(4-fluoro-2-methyl-phenyl)-piperidin-4-yl]-piperazine-1-carboxylic Acid Tert-butyl Ester (18b)

A solution of intermediate 10 (400 mg) and N-tert-butoxycarbonyl-piperazine (151.8 mg) in dry 1,2-dichloroethane (10 mL) was stirred at r.t. for 30 minutes under a nitrogen atmosphere. Then, sodium triacetoxyborohydride (0.310 mg) was added and the mixture was stirred at 23° C. for 24 hours. The solution was diluted with AcOEt and washed with water. The organic layer was dried and concentrated in vacuo to a residue, which was purified by flash chromatography (AcOEt/MeOH from 9:1) to give:

intermediate 18a (181 mg), intermediate 18b (155 mg).

Intermediate 18a:

T.l.c.: AcOEt/MeOH 8:2, Rf=0.35.

IR (nujol, cm$^{-1}$): 1703 and 1651 (C=O).

NMR (d$_6$-DMSO): δ (ppm) 7.91 (s, 1H); 7.65 (s, 2H); 7.26 (dd, 1H); 6.89 (dd, 1H); 6.79 (bt, 1H); 4.78 (dd, 1H); 4.52 (d, 1H); 4.37 (d, 1H); 3.25 (m, 6H); 3.09 (m, 1H); 2.78 (s, 3H); 2.37 (bs, 4H); 2.22 (s, 3H); 1.86 (m, 1H); 1.78 (m, 1H); 1.68 (m, 2H); 1.35 (s, 9H).

MS (ES/+): m/z=661 [MH]$^+$.

Intermediate 18b

T.l.c.: AcOEt/MeOH 8:2, Rf=0.14.

IR (nujol, cm$^{-1}$): 1702 and 1654 (C=O).

NMR (d$_6$-DMSO): δ (ppm) 7.90 (s, 1H); 7.56 (s, 2H); 7.18 (dd, 1H); 6.85 (dd, 1H); 6.73 (dt, 1H); 4.59 (d, 1H); 4.32 (d, 1H); 4.1 (dd, 1H); 3.41 (bm, 1H); 3.21 (bs, 4H); 2.87 (s, 3H); 2.64 (t, 1H); 2.5 (m, 1H); 2.39 (bs, 4H); 2.3 (s, 3H); 1.82 (bs, 1H); 1.73 (m, 1H); 1.56 (dq, 1H); 1.33 (s, 9H); 1.33 (q, 1H).

MS (ES/+): m/z=661 [MH]$^+$.

EXAMPLES 1a and 1b 2-(R)-(4-Fluoro-2-methyl-phenyl)-4-(R)-(3-oxo-piperazin-1-yl-)-piperidine-1-carboxylic Acid (3,5-bis-trifluoromethyl-benzyl)-methylamide (Example 1a) 2-(R)-(4-Fluoro-2-methyl-phenyl)-4-(S)-(3-oxo-piperazin-1-yl-)-piperidine-1-carboxylic Acid (3,5-bis-trifluoromethyl-benzyl)-methylamide (Example 1b)

Piperazin-2-one (60 mg) was added to a solution of intermediate 10 (150 mg) in dry 1,2-dichloroethane (3 mL) and dry acetonitrile (3 mL) under a Nitrogen atmosphere. The mixture was stirred at 23° C. for 16 hour, then sodium triacetoxyborohydride (97 mg) was added. The solution was stirred at 23° C. for 6 hours, then washed with a 5% sodium hydrogen carbonate solution (10 mL) and brine (10 mL). The organic layer was dried and concentrated in vacuo to a residue which was purified by flash chromatography (AcOEt/MeOH 9:1) to give two fractions:

1. example 1a (23 mg—T.l.c.: AcOEt/MeOH 8:2 Rf=0.24)
2. example 1b (56 mg—T.l.c.: AcOEt/MeOH 8:2 Rf=0.11).

EXAMPLE 1a

IR(nujol, cm$^{-1}$): 3350 (NH$^+$), 1734 and 1635 (C=O).

NMR (d$_6$-DMSO): δ (ppm) 7.94 (s, 1H); 7.78 (s, 1H); 7.66 (s, 2H); 7.30 (m, 1H); 6.93 (dd, 1H); 6.83 (m, 1H); 4.75 (dd, 1H); 4.58 (d, 1H); 4.40 (d, 1H); 3.3 (m, 2H); 3.10-3.00 (m, 4H); 3.83 (s, 3H); 2.70-2.50 (m, 3H); 2.27 (s, 3H); 2.00+1.60 (m, 4H).

MS (ES/+): m/z=575 [M+H]$^+$.

EXAMPLE 1b

IR (nujol, cm$^{-1}$): 3213 (NH$^+$), 1737 and 1657 (C=O).

NMR (d$_6$-DMSO): δ (ppm) 7.94 (s, 1H); 7.66 (s, 1H); 7.59 (s, 2H), 7.25 (dd, 1H); 6.89 (dd, 1H); 6.77 (m, 1H); 4.62 (d, 1H); 4.37 (d, 1H); 4.14 (dd, 1H); 3.46-3.04 (m, 4H); 2.90 (s, 3H); 1.88-1.36 (m, 4H).

MS (ES/+): m/z=1575 [M+H]$^+$.

EXAMPLE 2

2-(R)-(4-Fluoro-2-methyl-phenyl-4-(R)-(3-oxo-piperazin-1-yl-)-piperidine-1-carboxylic Acid (3,5-bis-trifluoromethyl-benzyl)methylamide Hydrochloride Hydrochloric acid (1M in Et$_2$O —0.3 mL) was added to a solution of example 1a (23 mg) in dry Et2O (3 mL) previously cooled to 0° C. under a nitrogen atmosphere. The resulting solution was stirred at 0° C. for 30 minutes, then it was concentrated in vacuo to give the title compound (18 mg) as a white solid.

NMR (d$_6$-DMSO): δ (ppm) 10.87 (bs, 1H); 8.46 (bs, 1H); 7.81 (s, 1H); 7.79 (s, 2H); 7.36 (m, 1H); 6.97 (m, 2H); 4.49 (q, 2H); 3.87-3.13 (bm, 9H); 2.76 (s, 3H); 2.25 (s, 3H); 2-0.5 (m, 4H).

MS (ES/+): m/z=575 [M+H–HCl]$^+$, 597 [M–HCl+Na]$^+$.

EXAMPLE 3

2-(R)-(4-Fluoro-2-methyl-phenyl)-4-(S)-(3-oxo-piperazin-1-yl-)-piperidine-1-carboxylic Acid (3,5-bis-trifluoromethyl-benzyl)-methylamide Hydrochloride Hydrochloric acid (1M in Et$_2$O —0.5 mL) was added to a solution of example 1b (56 mg) in dry Et$_2$O (5 mL) previously cooled to 0° C. under a nitrogen atmosphere. The resulting solution was stirred at 0° C. for 30 minutes, then it was concentrated in vacuo to give the title compound (46 mg) as a white solid.

IR (nujol, cm$^{-1}$): 3421 (NH$^+$), 1676 (C=O).

NMR (d$_6$-DMSO): δ (ppm) 10.84 (bs, 1H); 8.41 (s, 1H); 7.95 (s, 1H); 7.59 (s, 1H); 7.28 (m, 1 h) 6.92 (dd, 1H); 6.82 (m, 1H); 4.62 (d, 1H); 4.37 (d, 1H); 4.19 (dd, 1H); 3.9-3.2 (m, 7H); 2.82 (s, 3H); 2.75 (m, 1H); 2.37 (s; 3H); 2.25+2.7, (m, 4H).

MS (ES/+): m/z=575 [M+H–HCl]$^+$, 597 [M–HCl+Na]$^+$.

EXAMPLES 4a and 4b 2-(R)-(4-Fluoro-2-methyl-phenyl)-4-(R)-(4-methyl-3-oxo-piperazin-1-yl-)-piperidine-1-carboxylic Acid (3,5-bis-trifluoromethyl-benzyl)-methylamide (4a) 2-(R)-(4-Fluoro-2-methyl-phenyl)-4-(S)-(4-methyl-3-oxo-piperazin-1-yl-)- piperidine-1-carboxylic Acid (3,5-bis-trifluoromethyl-benzyl)-methylamide (4b)

TFA (0.8 mL) was added to a solution of intermediate 12 (190 mg) in DCM (8 mL) previously cooled to 0° C. under a nitrogen atmosphere. The mixture was stirred at r.t. for 4 hours, then it was concentrated in vacuo to give 1-methyl-piperazin-2-one trifluoroacetate (102 mg) which was used as a crude in the following reactions.

1-Methyl-piperazin-2-one trifluoroacetate (102 mg) and TEA (0.185 mL) were added to a solution of intermediate 10 (217 mg) in dry dichloroethane (6 mL) and dry acetonitrile (6 mL) under a nitrogen atmosphere. The mixture was stirred at 23° C. for 16 hours, then sodium triacetoxyborohydride (281 mg) was added and the solution was stirred for 6 hours. The mixture was washed with a 5% sodium hydrogen carbonate solution (10 mL) and brine (10 mL). The organic layer was dried and concentrated in vacuo, to a residue which was purified by flash chromatography (AcOEt/MeOH 9:1) to give two fractions:
1. example 4a (56 mg—T.l.c.: AcOEt/MeOH 8:2, Rf=0.33),
2. example 4b (42 mg—T.l.c.: AcOEt/MeOH 8:2, Rf=0.13).

EXAMPLE 4a

IR (nujol, cm$^{-1}$): 1649 (C=O).
NMR (d$_6$-DMSO): δ (ppm) 7.95 (bs, 1H); 7.66 (bs, 2H); 7.22; (dd, 1H); 6.93 (dd, 1H); 6.83 (dt, 1H); 4.72 (dd, 1H); 4.58 (d, 1H); 4.39 (d, 1H); 3.3-3.1 (m, 2H); 3.9-2.6 (m, 1H); 2.53 (m, 4H); 3.09 (m, 2H); 2.84 (s, 3H); 2.83 (s, 3H); 2.28 (s, 3H); 1.95-1.65 (m, 4H).
MS (ES/+): m/z=589 [M+H]$^+$.

EXAMPLE 4b

IR (nujol, cm$^{-1}$): 1650 (C=O).
NMR (d$_6$-DMSO): δ (ppm) 7.94 (bs, 1H); 7.59 (bs, 2H); 7.24 (dd, 1H); 6.90 (dd, 1H); 6.77 (dt, 1H); 4.62 (d, 1H); 4.37 (d, 1H); 4.13 (dd, 1H); 3.46 (m, 1H); 3.20 (m, 2H); 3.10 (m, 21); 2.91 (s, 3H); 2.78 (s, 3H); 2.80-2.50 (m, 4H); 2.35 (s, 3H); 1.89 (m, 1H); 1.83 (m, 1H); 1.61 (m, 1H); 1.34 (q, 1H).
MS (ES/+): m/z=589 [M+H]$^+$, 611 [M+Na]$^+$.

EXAMPLE 5

2-(R)-(4-Fluoro-2-methyl-phenyl)-4-(R)-(4-methyl-3-oxo-piperazin-1-yl-)-piperidine-1-carboxylic Acid (3,5-bis-trifluoromethyl-benzyl)methylamide Hydrochloride A solution of example 4a (56 mg) in dry Et$_2$O (5 mL) was treated with hydrochloric acid (1M in Et$_2$O —0.5 mL) and the resulting solution was stirred at 23° C. for 30 minutes. The solution was concentrated in vacuo to give the title compound as a white solid (26 mg).

IR (nujol, cm$^{-1}$): 1653 (C=O).
NMR (d$_6$-DMSO): δ (ppm) 11.10 (bs, 1H); 7.95 (s, 1H); 7.59 (s, 2H); 7.27 (bt, 1H); 6.93 (d, 1H); 6.82 (bt, 1H); 4.62 (d, 1H); 4.37 (d, 1H); 4.37 (d, 1H); 4.18 (d, 1H); 3.95-3.25 (m, 7H); 2.93 (s, 3H); 2.86 (s, 3H); 2.72 (t, 1H); 2.37 (s, 3H); 2.20-2.08 (m, 2H); 1.90 (bm 1H); 1.8-1.6 (bm, 1H).
MS (ES/+): m/z=589 [MH–HCl], 611 [M–HCl+Na]$^+$.

EXAMPLE 6

2-(R)-(4-Fluoro-2-methyl-phenyl)-4-(S)-4-methyl-3-oxo-piperazin-1-yl-)-piperidine-1-carboxylic Acid (3.5-bis-trifluoromethyl-benzyl)-methylamide Hydrochloride A solution of example 4b (42 mg) in dry Et$_2$O (4 mL) was treated with hydrochloric acid (1M in Et$_2$O—0.4 mL) and the resulting solution was stirred at 23° C. for 30 minutes. The solution was concentrated in vacuo to give the title compound (28 mg) as a white solid.

IR (nujol, cm$^{-1}$): 3395 (NH$^+$), 2800-2500 (NH), 1665 (C=O), 1623 (C=C).
NMR (d$_6$-DMSO): δ (ppm) 10.93 (bs, 1H); 7.98 (bs, 1H); 7.78 (bs, 2H); 7.36 (bm, 1H); 7.01 (bm, 1H); 6.92 (bm, 1H); 5.19 (bm, 1H); 4.59 (d, 1H); 4.41 (d, 1H); 4.1-3 (bm, 9H); 2.89 (s, 3H); 2.76 (s, 3H); 2.5-2.0 (bm, 6H); 1.80 (bm, 1H).
MS (ES/+): m/z=589 [MH–HCl]$^+$.

EXAMPLE 7

2-(R)-(4-Fluoro-2-methyl-phenyl)-4-(S)-(4-methyl-3-oxo-piperazin-1-yl)-piperidine-1-carboxylic Acid [1-(R)-(3,5-bis-trifluoromethyl-phenyl)-ethyl]-methylamide Hydrochloride TFA (1 mL) was added to a solution of intermediate 12 (210 mg) in DCM (9 mL) previously cooled to 0° C. under a nitrogen atmosphere. The mixture was stirred at r.t. for 4 hours, then was concentrated in vacuo to give 1-methyl-piperazin-2-one trifluoroacetate (210 mg) which was dissolved in DCM (10 mL) and the mixture treated with solid potassium carbonate. The inorganic material was filtered off and the solution was concentrated in vacuo to give 1-methyl-piperazin-2-one (111 mg). The residue was added to a solution intermediate 4b (245 mg) in dry 1,2-dichloroethane (4 mL) and dry acetonitrile (4 mL) under a nitrogen atmosphere. The mixture was stirred at 23° C. for 16 hours, then sodium triacetoxyborohydride (354 mg) was added. The solution was stirred at 23° C. for 3 days, then washed with a 5% sodium hydrogen carbonate solution (10 mL) and brine (10 mL). The organic layer was dried and concentrated in vacuo to a residue which was purified by flash chromatography (AcOEt/MeOH 98:2) to give three fractions:
1. diastereoisomer 1 (C-2 and C-4 anti configuration—9 mg—T.l.c.: AcOEt/MeOH 9:1, Rf=0.27).
2. mixture of the two diastereoisomers (104 mg).
3. diastereoisomer 2 (C-2 and C-4 syn configuration—24 mg—T.l.c.: AcOEt/MeOH 9:1, Rf=0.22).

A solution of diastereoisomer 2 (24 mg) in dry Et$_2$O (1 mL) was treated with hydrochloric acid (1M in Et$_2$O —0.2 mL). The resulting solution was stirred at 0° C. for 30 minutes, then it was concentrated in vacuo to give the title compound (13 mg) as a white solid.

NMR (d$_6$-DMSO, 70° C.): δ (ppm) 11 (bs, 1H); 7.92 (s, 1H); 7.67 (s, 2H); 7.23 (dd, 1H); 6.90 (dd, 1H); 6.79 (m, 1H); 5.32 (q, 1H); 4.21 (dd, 1H); 3.5-2.8 (m, 9H); 2.10 (m, 2H); 1.8 (m, 1H); 1.7 (m, 1H); 2.86 (s, 3H); 2.74 (s, 3H); 2.37 (s, 3H); 1.47 (d, 3H).
MS (ES/+): m/z=603 [M+H–HCl]$^+$.

EXAMPLE 8

2-(R)-(4-Fluoro-2-methyl-phenyl)-4-(R)-(2-oxo-piperazin-1-yl)-piperidine-1-carboxylic Acid (3,5-bis-trifluoromethyl-benzyl)methylamide Hydrochloride Bromoacetylbromide (5 μL) and TEA (13 μL) were added to a solution of intermediate 13a (29 mg) in dry DCM (0.5 mL) previously cooled to 0° C. under a nitrogen atmosphere. The solution was stirred at 0° C. for 30 minutes, then it was washed with brine. The organic layer was dried and concentrated in vacuo to give {2-[1-(3,5-bis-trifluoromethyl-benzyl)-methyl-carbamoyl]-2-(R)-(4-fluoro-2-methyl-phenyl)-piperidin-4-(R)-yl]-2-bromo-acetyl)-amino-ethyl}-carbamic acid tert-butyl ester (28 mg), which was used without further purification in the next reactions.

TFA (0.1 mL) was added to a solution of this material (28 mg) in dry DCM (0.9 mL), previously cooled to 0° C. under a nitrogen atmosphere. The mixture was stirred at 23° C. for 1 hour. The organic layer was washed with a saturated solution of sodium hydrogen carbonate (1 mL) and brine (1 mL), then dried. After concentration in vacuo, the residue was purified by flash chromatography (AcOEt/MeOH 9:1) to give of 2-(R)-(4-fluoro-2-methyl-phenyl)-4-(R)-(2-oxo-piperazin-1-yl)-piperidine-1-carboxylic acid (3,5-bis-trifluoromethyl-benzyl)-methylamide (11 mg).

This material (11 mg) was dissolved in dry $Et_2O$ (1 mL) and treated with hydrochloric acid (1M in $Et_2O$ —0.1 mL). The resulting solution was stirred at 23° C. for 30 minutes, then concentrated in vacuo to give the title compound (6 mg) as a white solid.

NMR ($d_6$-DMSO): δ (ppm) 9.19 (bs, 2H); 8.00 (s, 1H); 7.88 (s, 2H); 5.75 (m, 1H); 7.24-6.98 (m, 1H); 5.31 (bs, 1H); 4.8 (bs, 1H); 4.56 (d, 1H); 4.46 (d, 1H); 3.6 (m, 1H); 3.4 (m, 6H); 3.00 (m, 1H); 2.73 (s, 3H); 2.16 (s, 3H); 2.1 (m, 1H); 1.9 (m, 1H); 1.6 (m, 2H). MS (ES/+): m/z=575 [M+H−HCl]$^+$.

EXAMPLE 9

2-(R)-(4-Fluoro-2-meth-phenyl)-4-(S)-(2-oxo-piperazin-1-yl-piperidine-1-carboxylic Acid (3,5-bis-trifluoromethyl-benzyl)-methylamide Bromoacetylbromide (7 μL) and TEA (18 μL) were added to a solution of intermediate 13b (41 mg) in dry DCM (0.6 mL) previously cooled to 0° C. under a nitrogen atmosphere. The solution was stirred at 0° C. for 30 minutes. The organic layer was washed with brine, dried and concentrated in vacuo to give {2-[1-(3,5-bis trifluoromethyl-benzyl)-methyl-carbamoyl]-2-(R)-(4-fluoro-2-methyl-phenyl)-piperidin-4-(S)-yl]-2-bromo-acetyl)amino-ethyl}-carbamic acid tert-butyl ester (19 mg), which was used without further purification for the next reaction.

TFA (0.05 mL) was added to a solution of this material (18 mg) in dry DCM (0.45 mL), previously cooled to 0° C. under a nitrogen atmosphere. The mixture was stirred at 23° C. for 1 hour. The organic layer was washed with a saturated solution of sodium hydrogen carbonate (1 mL) and brine (1 mL), then dried. The residue was purified by flash chromatography (AcOEt/MeOH 8:2) to give the title compound (5.5 mg) as a white foam.

MS (ES/+): m/z=575 [M+H]$^+$.

EXAMPLE 10

2-(4-Fluoro-2-methyl-phenyl)-4-(S)-(2-oxo-piperazin-1-yl)-piperidine-carboxylic Acid (3,5-bis-trifluoromethyl-benzyl)-methylamide Hydrochloride Hydrochloric acid (1M in $Et_2O$ —0.05 mL) was added to a solution of example 9 (5.5 mg) in dry $Et_2O$ (0.5 mL) previously cooled to 0° C. under a nitrogen atmosphere. The resulting solution was stirred at 0° C. for 30 minutes, then concentrated in vacuo to give the title compound (3 mg) as a white solid.

NMR ($d_6$-DMSO): δ (ppm) 9.19 (bs, 2H); 8.0 (s, 1H); 7.88 (s, 2H); 5.75 (m, 1H); 7.24-6.98 (m, 1H); 5.31 (bs, 1H); 4.8 (bs, 1H); 4.56 (d, 1H); 4.46 (d, 1H); 3.6 (m, 1H); 3.4 (m, 6H); 3.0 (m, 1H); 2.73 (s, 3H); 2.16 (s, 3H); 2.1 (m, 1H); 1.9 (m, 1H); 1.6 (m, 2H).

MS (ES/+): m/z=575 [M+H−HCl]$^+$.

EXAMPLE 11

2-(R)-(4-Fluoro-2-methyl-phenyl)-4-(S)-(2-oxo-4-methyl-piperazin-1-yl)-piperidine-1-carboxylic Acid (3,5-bis-trifluoromethyl-benzyl)-methylamide Formaldehyde (37% in water, 0.093 mL) was added to a solution example 9 (270 mg) in 1,2-dichloroethane (4 mL). The mixture was stirred for 15 minutes at room temperature, then sodium triacetoxyborohydride (149 mg) was added. The solution was stirred for 3 hours at 23° C., then it was washed with 5% sodium hydrogen carbonate solution (10 mL) and brine. The organic layer was dried and concentrated in vacuo to a residue which was purified by flash chromatography (AcOEt/MeOH 8:2) to give 2-(R)-(4-fluoro-2-methyl-phenyl)-4-(S)-(2-oxo-4-methyl-piperazin-1-yl)-piperidine-1-carboxylic acid, (3,5-bis-trifluoromethyl-benzyl)-methylamide (120 mg).

This material (120 mg) was dissolved in dry $Et_2O$ (2 mL) and treated with hydrochloric acid (1M in $Et_2O$ —0.4 mL). The resulting solution was stirred at 0° C. for 30 minutes, then it was concentrated in vacuo to give the title compound (90 mg) as a white solid.

IR (nujol, cm$^{-1}$): 1653 (C=O).

NMR ($d_6$-DMSO):δ (ppm) 10.6 (bs, 1H); 7.95 (s, 1H); 7.60 (2.25, 2H); 7.28 (dd, 1H); 6.92 (dd, 1H); 6.80 (t, 1H); 4.64 (d, 1H); 4.44 (t, 1H); 4.38 (d, 1H); 4.23 (dd, 1H); 4-3.2 (bm, 5H); 2.92 (s, 3I); 2.8 (m, 2H); 2.9-2.5 (sb, 3H); 2.34 (s, 3H); 1.98 (m, 2H); 1.75-1.55 (m, 2H).

MS (ES/+): m/z=589 [M+H−HCl]$^+$.

EXAMPLE 12

2-(R)-(4-Fluoro-2-methyl-phenyl) (S)-(4-methyl-2-oxo-piperazin-1-yl)-piperidine-1-carboxylic Acid [1-(R)-(3,5-bis-trifluoromethyl-phenyl)-ethyl]-methylamide Bromoacetylbromide (0.027 mL) and TEA (0.073 mL) were added to a solution of intermediate 14b (162 mg) in dry dichloromethane (2 mL) previously cooled to 0° C. under a nitrogen atmosphere. The solution was stirred at 0° C. for 30 minutes. The organic layer was washed with brine, dried and the solution concentrated in vacuo to give {2-[1-{[1-(3,5-bis-trifluoromethyl-phenyl)-ethyl]-methyl-carbamoyl}-2 (R)-(4-fluoro-2-methyl-phenyl)-piperidin-4-(S)-yl]-2-bromo-acetyl)-amino]-ethyl}-carbamic acid tert-butyl ester (200 mg), which was used without further purification in the next reaction.

TFA (0.2 mL) was added to a solution of this compound (200 mg) in dry dichloromethane (1.8 mL) previously cooled to 0° C. under a nitrogen atmosphere. The mixture was stirred at 23° C. for 3 hours, then washed with a saturated solution of sodium hydrogen carbonate (1 mL) and brine (1 mL), then dried and concentrated in vacuo. The residue was purified by flash chromatography (AcOEt/ MeOH 8:2) to give the title compound (49 mg).

NMR ($d_6$-DMSO): δ (ppm) 7.75 (bs, 1H); 7.55 (bs, 2H); 7.15 (dd, 1H); 6.8 (m, 2H); 5.55 (q, 1H); 4.7 (bm, 1H); 4.35 (dd, 1H); 3.6-2.9 (m, 6H); 2.7 (s, 3H); 2.4 (s, 3H); 2.5-2.0 (bm, 2H); 2.0-1.5 (m, 4H); 1.4 (d, 3H).

EXAMPLE 13

2-(R)-(4-Fluoro-2-methyl-phenyl)-4-(S)-(4-methyl-2-oxo-piperazin-1-yl)-piperidine-1-carboxylic Acid [1-(R)-(3,5-bis-trifluoromethyl-phenyl)-ethyl]-methylamide Hydrochloride Formaldehyde (37% in water, 0.012 mL) was added to a solution of example 12 (49 mg) in acetonitrile (8 mL). The mixture was stirred for 30 minutes at room temperature, then sodium triacetoxyborohydride (26 mg) was added. The solution was stirred for 4 hours at 23° C. and concentrated in vacuo. The residue was dissolved in DCM and the organic layer washed with 5% sodium hydrogen carbonate solution (10 mL) and brine, then dried and concentrated in vacuo. The residue was purified by flash chromatography (AcOEt/ MeOH 9:1) to give 2-(R)-(4-fluoro-2-methyl-phenyl)-4-(S)-(4-methyl-2-oxo-piperazin-1-yl)-piperidine-1-carboxylic acid [1 (R)-(3,5-bis-trifluoromethyl-phenyl)-ethyl]-methylamide (22 mg).

This material (22 mg) was dissolved in dry $Et_2O$ (2.5 mL) and treated with hydrochloric acid (1M in $Et_2O$—0.2 mL). The solution was stirred at 0° C. for 30 minutes, then it was concentrated in vacuo to give the title compound (18 mg) as a white solid.

NMR ($d_6$-DMSO): δ (ppm) 10.82 (bs, 1H); 7.96 (s, 1H); 7.55 (s, 2H); 7.18 (dd, 1H); 6.86 (dd, 1H); 6.75 (dt, 1H); 5.3 (q, 1H); 4.41 (bt, 1H); 4.18 (dd, 1H); 3.9-3.4 (many bs, 6H); 3.37 (m, 1H); 2.8 (m, 1H); 2.74 (bs, 3H); 2.69 (bs, 3H); 2.3 (bs, 3H); 1.93 (m, 1H); 1.75 (q, 1H); 1.63 (bd, 1H); 1.54 (bd, 1H); 1.43 (d, 3H).

MS (ES/+): m/z=603 [M+H−HCl]$^+$.

EXAMPLES 14a and 14b 2-(R)-(4-Fluoro-2-methyl-phenyl)-4-(R)-(4-cyclopropyl-3-oxo-piperazin-1-yl-)-piperidine-1-carboxylic Acid 1-(3,5-bis-trifluoromethyl-benzyl)-methylamide Hydrochloride (14a) 2-(R)-(4-Fluoro-2-methyl-phenyl)-4-(S)-(4-cyclopropyl-3-oxo-piperazin-1-yl-)-piperidine-1-carboxylic Acid 1-(3,5-bis-trifluoromethyl-benzyl)-methylamide Hydrochloride (14b)

TFA (2.5 mL) was added to a solution of intermediate 17 (254 mg) in anhydrous DCM (7.5 mL) previously cooled to 0° C. under a nitrogen atmosphere. The solution was allowed to warm to r.t. and stirred at 23° C. for 1 hour. The solution was concentrated in vacuo to give the crude 1-cyclopropyl-piperazine trifluoroacetate (269 mg), which was used without any further purification.

TEA (443 µL) and a solution of 1-cyclopropyl-piperazine trifluoroacetate (269 mg) in 1,2-dichloroethane (5 mL) were added to a solution of intermediate 10 (486 mg) in dry 1-2-dichloroethane (20 mL) under a nitrogen atmosphere. The resulting mixture was stirred at r.t. for 30 minutes, then sodium triacetoxyborohydride (334 mg) was added and the resulting mixture was stirred at 23° C. for 16 hours. A 5% sodium hydrogen carbonate solution (20 mL) was added, the layers were separated and the aqueous layer was extracted with further DCM (20 mL). The combined extracts were dried and concentrated in vacuo. The residue was purified by flash chromatography (from AcOEt to AcOEt/MeOH 95:5) to give two fractions: -diastereoisomer 1 (106 mg—T.l.c. AcOEt/MeOH 95:5, Rf=0.18) -diastereoisomer 2 (220 mg—T.l.c. AcOEt/MeOH 95:5, Rf=0.09).

EXAMPLE 14a

A solution of diastereoisomer 1 (99 mg) in dry $Et_2O$ (2 mL) was treated with hydrochloric acid (1M in $Et_2O$—0.177 mL) at 0° C. and the resulting mixture was stirred at 0° C. for 30 minutes. The solution was concentrated in vacuo and the residue was triturated with pentane to give the title compound as a yellow solid (70 mg).

NMR ($d_6$-DMSO): δ (ppm) 10.66 (bs, 1H); 7.98 (bs, 1H); 7.78 (bs, 2H); 7.35 (bm, 1H); 6.99 (bm, 1H); 6.92 (bm, 1H); 5.17 (bm, 1H); 4.58 (d, 1H); 4.41 (d, 1H); 4.0-2.73 (many bm, 10H); 2.76 (s, 3H); 2.25 (s, 3H); 2.16 (bm, 2H); 1.77 (bm, 2H); 0.74 (bs, 2H); 0.65 (bs, 2H).

MS (ES/+): m/z=614 [M+H−HCl]$^+$.

EXAMPLE 14b

A solution of diastereoisomer 2 (149 mg) in dry $Et_2O$ (3 mL) was treated with hydrochloric acid (1M in $Et_2O$—0.27 mL) at 0° C. and the resulting mixture was stirred at 0° C. for 30 minutes. The solution was concentrated in vacuo and the residue was triturated with pentane to give the title compound as a white solid (115 mg).

NMR ($d_6$-DMSO): δ (ppm) 11.23 (bs, 1H); 7.95 (s, 1H); 7.58 (s, 2H); 7.28 (m, 1H); 6.94 (dd, 1H); 6.82 (dt, 1H); 4.62 (d, 1H); 4.37 (d, 1H); 4.18 (bd, 1H); 4.0-3.0 (bm, 8H); 2.92 (s, 3H); 2.7 (m, 2H); 2.37 (s, 3H); 2.2-1.6 (bm, 4H); 0.72 (bd, 2H); 0.63 (bd, 2H).

MS (ES/+): m/z=614 [M+H−HCl]$^+$.

EXAMPLE 15

2-(R)-(4-Fluoro-2-methyl-phenyl)-4-(S)(1-methanesulfo-nyl-piperazin-1-yl)-piperidine-1-carboxylic acid 1-(3,5-bis-trifluoromethyl-benzyl)-methylamide TFA (1 mL) was added to a solution of intermediate 18b (155 mg) in anhydrous DCM (5 mL). The solution was stirred at r.t. for 3 hours, then it was concentrated in vacuo. The residue was diluted in a saturated potassium carbonate solution (10 mL) and extracted with DCM (2×20 mL) and AcOEt (20 mL). The combined organic extracts were dried and concentrated in vacuo to give 4-(S)-[1-[(3,5-Bis-trifluoromethyl-benzyl)-methyl-carbamoyl]-2(R)-(4-fluoro-2-methyl-phenyl)-piperidin-4-yl]-piperazine (104 mg) as an oil.

T.l.c.: AcOEt/MeOH 8:2, Rf=0.12. IR (nujol, cm$^{-1}$): 1653 (C=O).

NMR ($d_6$-DMSO): δ (ppm) 7.94 (s, 1H); 7.59 (s, 2H); 7.22 (dd, 1H); 6.89 (dd, 1H); 6.77 (dt, 1H); 4.62 (d, 1H); 4.36 (d, 1H); 4.13 (dd, 1H); 3.44 (dt, 1H); 3.3 (m, 1H); 2.9 (s, 3H); 2.67 (m, 1H); 2.65 (m, 4H); 2.4 (bm, 4H); 2.34 (s, 3H); 1.86 (bd, 1H); 1.77 (bd, 1H); 1.6 (dq, 1H); 1.34 (q, 1H). MS (ES/+): m/z=561 [MH]$^+$.

80 mg of such an oil was dissolved in in anhydrous DCM (3 mL) the solution was cooled at 0° C. under a nitrogen atmosphere and then methanesulfonyl chloride (11.8 µL)

Methanesulfonyl chloride (11.8 μL) and TEA (40 μL) were added to a solution The solution was stirred at 0° C. for 4 hours, then it was washed with saturated sodium hydrogen carbonate solution (5 mL). The layers were separated and the organic phase was extracted with further DCM (3×5 mL). The combined organic extracts were dried and concentrated in vacuo to a residue, which was purified by flash chromatography (AcOEt/MeOH 9:1) to give the title compound (60 mg) as a colourless oil.

T.l.c.: AcOEt/MeOH 9:1, Rf=0.27.

NMR ($d_6$-DMSO): δ (ppm) 7.93 (s, 1H); 7.59 (s, 2H); 7.23 (dd, 1H); 6.89 (dd, 1H); 6.77 (dt, 1H); 4.62 (d, 1H); 4.36 (d, 1H); 4.14 (dd, 1H); 3.46 (m, 1H); 3.3 (m, 1H); 3.04 (m, 4H); 2.9 (s, 3H); 2.83 (s, 3H); 2.67 (t, 1H); 2.5 (m, 4l); 2.34 (s, 3M); 1.9-1.75 (m, 2H); 1.65 (m, 1H); 1.38 (m, 1H).

MS (ES/+): m/z=639 $[MH]^+$.

EXAMPLE 16

2-(R)-(4-Fluoro-2-methyl-phenyl)-4-(S)(1-methanesulfonyl-piperazin-1-yl)-piperidine-1-carboxylic Acid (3,5-bis-trifluoromethyl-benzyl)-methylamide Hydrochloride A solution of example 17 (58 mg) in dry $Et_2O$ (2 mL) was treated with hydrochloric acid (1M in $Et_2O$—0.1 mL) at 0° C. and the resulting mixture was stirred at 0° C. for 30 minutes. The solution was concentrated in vacuo and the residue was triturated with pentane to give the title compound as a white solid (53 mg).

NMR ($d_6$-DMSO): 6 (ppm) 10.09 (bs, 1H); 7.96 (bs, 1H); 7.61 (bs, 2H); 7.27 (m, 1H); 6.96 (m, 1H); 6.84 (m, 1H); 4.64 (d, 1H); 4.37 (d, 1H); 4.22 (d, 1H); 3.8-3.5 (m, 2H); 3.5-2.9 (m, 8H); 3.02 (s, 3H); 2.94 (s, 3H); 2.76 (m, 1H); 2.38 (m, 3H); 2.17 (m, 2H); 1.88 (m, 1H); 1.69 (m, 1H).

MS (ES/+): m/z=639 $[MH-HCl]^+$.

EXAMPLE 17

2-(R)-(4-Fluoro-2-methyl-phenyl)-4-(S)(1-methanesulfonyl-piperazin-1-yl)-piperidine-1-carboxylic Acid [1-(R)-(3,5-bis-trifluoromethyl-phenyl)-ethyl]-methylamide A solution of intermediate 4a (160 mg), N-tert-butoxycarbonyl-piperazine (60 mg) and sodium triacetoxyborohydride (100 mg) in dry 1,2-dichloroethane (12 mL) was stirred at 23° C. for 24 hours under a nitrogen atmosphere. The solution was washed with a 5% sodium hydrogen carbonate solution (20 mL) and brine (20 mL). The organic layer was dried and concentrated in vacuo to a residue, which was purified by flash chromatography (CH/AcOEt from 1:1 to 3:7) to give:

2-(R)-(4-Fluoro-2-methyl-phenyl)-4-(R)-[(4-tert-butoxycarbonyl)-piperazin-1-yl]-piperidine-1-carboxylic acid [1-(R)3,5-bis-trifluoromethyl-phenyl)ethyl]-methylamide (74 mg —T.l.c.: CH/AcOEt 1:1, Rf=0.35 hereinafter compound 1)

-2-(R)-(4-Fluoro-2-methyl-phenyl)-4-(S)-[(4-tert-butoxycarbonyl)-piperazin-1-yl]-piperidine-1-carboxylic acid [1-(R)3,5-bis-trifluoromethyl-phenyl)-ethyl]-methylamide (48 mg—T.l.c.: CH/AcOEt 1:1, Rf=0.19 hereinafter compound 2).

Trifluoroacetic acid (1 mL) was added drop-wise at 0° C. to a solution of compound 2 (48 mg) in dry DCM (3 mL). The solution was stirred for 1 hour at the same temperature and for 1 hour at r.t. Then the solvent was removed in vacuo and the crude dissolved in AcOEt (5 mL). The resulting solution was washed with a saturated potassium carbonate solution and dried. After concentration in vacuo, the crude 2-(R)-(4-fluoro-2-methyl-phenyl)-4-(S)-piperazin-1-yl-piperidine-1-carboxylic acid [1-(R)-(3,5-bis-trifluoromethylphenyl)-ethyl]-methylamide (18 mg) was obtained.

Methanesulfonyl chloride (6 μL) and TEA (20 μL) were added to a solution of this intermediate (40 mg) in anhydrous DCM (3 mL) previously cooled to 0° C. under a Nitrogen atmosphere. The solution was stirred at 0° C. for 4 hours, then it was washed with saturated sodium hydrogen carbonate solution (5 mL). The layers were separated and the organic phase was extracted with further DCM (3×5 mL). The combined organic extracts were dried and concentrated in vacuo to a residue, which was purified by flash chromatography (AcOEt/CH 94:6) to give the title compound (26 mg) as a colourless oil.

T.l.c.: AcOEt/CH 96:4, Rf=0.15.

NMR ($d_6$-DMSO): δ (ppm) 7.98 (s, 1H); 7.67 (s, 2H); 7.16 (dd, 1H); 6.89 (dd, 1H); 6.74 (dt, 1H); 5.32 (q, 1H); 4.13 (dd, 1H); 3.39 (m, 1H); 3.3 (m, 1H); 3.04 (m, 4H); 2.82 (s, 3H); 2.7 (s, 4H); 2.56 (m, 4H); 2.33 (s, 3H); 1.9-1.4 (m, 4H); 1.45 (d, 3H).

MS (ES/+): m/z=653 $[MH]^+$.

EXAMPLE 18

2-(R)-(4-Fluoro-2-methyl-phenyl)-4-(S)-(1-methanesulfonyl-piperazin-1-yl)-piperidine-1-carboxylic Acid 1-[(R)-(3,5-bis-trifluoromethyl-phenyl)-ethyl]-methylamide Hydrochloride A solution of example 18 (24.7 mg) in dry $Et_2O$ (1.5 mL) was treated with hydrochloric acid (1M in $Et_2O$ —0.042 mL) at 0° C. and the resulting mixture was stirred at 0° C. for 30 minutes. The solution was concentrated in vacuo and the residue was triturated with pentane to give the title compound as a white solid (22 mg).

NMR ($d_6$-DMSO): δ (ppm) 10.62 (bs, 1H); 7.98 (s, 1H); 7.67 (s, 2H); 7.21 (dt, 1H); 6.94 (dd, 1H); 6.82 (dt, 1H); 5.3 (q, 1H); 4.18 (dd, 1H); 3.8-3.45 (m, 5H); 3.3-3.1 (m, 5H); 2.99 (s, 3H); 2.73 (s, 3H); 2.7 (t, 1H); 2.35 (s, 3H); 2.2 (m, 2H); 1.9-1.7 (m, 2 h); 1.46 (d, 3H).

MS (ES/+): m/z=653 $[MH-HCl]^+$.

Pharmacy Examples

A. Tablets

| | |
|---|---|
| Active ingredient | 10.0 mg |
| PVP | 9 mg |
| Microcrystalline Cellulose | 266 mg |
| Sodium Starch Glycolate | 12 mg |
| Magnesium Stearate | 3 mg |
| Active ingredient | 50 mg |
| PVP | 9 mg |
| Microcrystalline Cellulose | 226 mg |
| Sodium Starch Glycolate | 12 mg |
| Magnesium Stearate | 3 mg |

The active ingredient is blended with the other excipients. The blend can be compressed to form tablets using appropriate punches. The tablets can be coated using conventional techniques and coatings.

B. Capsules

| Active ingredient | 25.0 mg |
| --- | --- |
| | (1-100 mg) |
| Microcrystalline Cellulose | qs |

The active ingredient is blended with microcrystalline cellulose and then filled into suitable capsules.

C. Injection

| Active ingredient | 2-20 mg/mL |
| --- | --- |
| Buffer solution pH 3.5 (3.0-4.0) suitable for injection (e.g. citrate buffer in sterile water for injection or NaCl 0.9%) | qs to 10 mL |

The formulation may be packaged in glass or plastic vials or ampules. The formulation may be administered by bolus injection or infusion, e.g. after dilution with D5W or 0.9% NaCl.

The affinity of the compound of the invention for $NK_1$ receptor was determined using the $NK_1$ receptor binding affinity method measuring in vitro by the compounds' ability to displace [3H]—substance P (SP) from recombinant human $NK_1$ receptors expressed in Chinese Hamster Ovary (CHO) cell membranes. The affinity values are expressed as negative logarithm of the inhibition constant (Ki) of displacer ligands (pKi).

The pki values obtained as the average of at least two determinations with representative compounds of the invention are within the range of 9.80 to 10.5.

The invention claimed is:

1. A compound of formula (I)

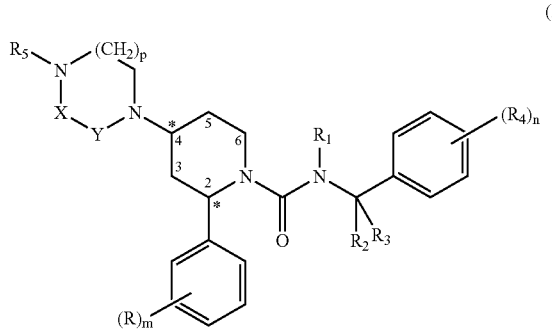

(I)

wherein
R is halogen or $C_{1-4}$ alkyl;
$R_1$ is hydrogen or $C_{1-4}$ alkyl;
$R_2$ is hydrogen, $C_{1-4}$ alkyl;
$R_3$ is hydrogen, $C_{1-4}$ alkyl;
$R_4$ is trifluoromethyl, $C_{1-4}$ alkyl, $C_{1-4}$ alkoxy, trifluoromethoxy or halogen;
$R_5$ is hydrogen, $C_{1-4}$ alkyl, $C_{3-7}$ cycloalkyl, $C(O)R_6$ or $S(O)_2R_6$;
$R_6$ is $C_{1-4}$ alkyl or $C_{3-7}$ cycloalkyl;
m is zero or an integer from 1 to 3;
n is an integer from 1 to 3;
p is an integer from 1 to 2;
X and Y are independently C(O) or $CH_2$;
provided that i) X and Y are not both C(O) and
ii) when X and Y are both $CH_2$ and p is 1, $R_5$ is not hydrogen, $C_{1-4}$ alkyl or $C(O)R_6$;
or a pharmaceutically acceptable salt thereof.

2. A compound as claimed in claim 1 wherein m is zero or an integer from 1 to 2.

3. A compound as claimed in claim 1 wherein $R_1$ is a methyl group.

4. A compound as claimed in claim 1 wherein $R_2$ is a hydrogen atom or a methyl group.

5. A compound as claimed in claim 1 wherein $R_3$ is a hydrogen atom or a methyl group.

6. A compound as claimed in claim 1 wherein $R_4$ is a trifluoromethyl group or halogen.

7. A compound as claimed in claim 1 wherein $R_5$ is hydrogen, methyl cyclopropyl, $C(O)CH_3$ or $S(O)_2CH_3$.

8. A compound as claimed in claim 1 wherein p is 1.

9. A compound as claimed in claim 1 wherein R is at the 2 and/or 4 position in the phenyl ring.

10. A compound as claimed in claim 1 wherein n is 2 and the groups $R_4$ are at the 3 and 5 position in the phenyl ring.

11. A compound as claimed in claim 1 wherein
R is fluorine and/or $C_{1-4}$ alkyl;
$R_1$ is a methyl group;
$R_2$ is a hydrogen atom or a methyl group;
$R_3$ is a hydrogen atom or a methyl group;
$R_4$ is trifluoromethyl;
$R_5$ is hydrogen, methyl, cyclopropyl, $C(O)CH_3$ or $S(O)_2CH_3$;
m is 1 or 2;
n is 2;
p is 1.

12. A compound selected from
2-(R)-(4-Fluoro-2-methyl-phenyl)-4-(R)-(3-oxo-piperazin-1-yl-)-piperidine-1-carboxylic acid, (3,5-bis-trifluoromethyl-benzyl)-methylamide;
2-(R)-(4-Fluoro-2-methyl-phenyl)-4-(S)-(3-oxo-piperazin-1-yl-)-piperidine-1-carboxylic acid, (3,5-bis-trifluoromethyl-benzyl)-methylamide;
2-(R)-(4-Fluoro-2-methyl-phenyl)-4-(R)-(4-methyl-3-oxo-piperazin-1-yl-)-piperidine-1-carboxylic acid, 1-(3,5-bis-trifluoromethyl-benzyl)-methylamide;
2-(R)-(4-Fluoro-2-methyl-phenyl)-4-(S)-(4-methyl-3-oxo-piperazin-1-yl-)-piperidine-1-carboxylic acid, 1-(3,5-bis-trifluoromethyl-benzyl)-methylamide;
2-(R)-(4-Fluoro-2-methyl-phenyl)-4-(S)-(4-methyl-3-oxo-piperazin-1-yl)-piperidine-1-carboxylic acid, [1-(R)-(3,5-bis-trifluoromethyl-phenyl)-ethyl]-methylamide;
2-(R)-(4-Fluoro-2-methyl-phenyl)-4-(R)-(2-oxo-piperazin-1-yl)-piperidine-1-carboxylic acid (3,5-bis-trifluoromethyl-benzyl)-methylamide;
2-(4-Fluoro-2-methyl-phenyl)-4-(S)-(2-oxo-piperazin-1-yl)-piperidine-1-carboxylic acid, (3,5-bis-trifluoromethyl-benzyl)-methylamide;
2-(4-Fluoro-2-methyl-phenyl)-4-(S)-(2-oxo-piperazin-1-yl)-piperidine-1-carboxylic acid, (3,5-bis-trifluoromethyl-benzyl)-methylamide;
2-(R)-(4-Fluoro-2-methyl-phenyl)-4-(S)-(2-oxo-4-methyl-piperazin-1-yl)-piperidine-1-carboxylic acid, (3,5-bis-trifluoromethyl-benzyl)-methylamide;
2-(R)-(4-Fluoro-2-methyl-phenyl)-4-(S)-(4-methyl-2-oxo-piperazin-1-yl)-piperidine-1-carboxylic acid, [1-(R)-(3,5-bis-trifluoromethyl-phenyl)-ethyl]-methylamide;

2-(R)-(4-Fluoro-2-methyl-phenyl)-4-(S)-(4-methyl-2-oxo-piperazin-1-yl)-piperidine-1-carboxilic acid, [1-(R)-(3,5-bis-trifluoromethyl-phenyl)-ethyl]-methylamide;

2-(R)-(4-Fluoro-2-methyl-phenyl)-4-(R)-(4-cyclopropyl-3-oxo-piperazin-1-yl-)-piperidine-1-carboxylic acid, 1-(3,5-bis-trifluoromethyl-benzyl)-methylamide;

2-(R)-(4-Fluoro-2-methyl-phenyl)-4-(S)-(4-cyclopropyl-3-oxo-piperazin-1-yl-)-piperidine-1-carboxylic acid, 1-(3,5-bis-trifluoromethyl-benzyl)-methylamide;

2-(R)-(4-Fluoro-2-methyl-phenyl)-4-(S)-(1-methane-sulfonyl-piperazin-1-yl)-piperidine-1-carboxylic acid, 1-(3,5-bis-trifluoromethyl-benzyl)-methylamide;

2-(R)-(4-Fluoro-2-methyl-phenyl)-4-(S)-(1-methane-sulfonyl-piperazin-1-yl)-piperidine-1-carboxylic acid, 1-[(R)-(3,5-bis-trifluoromethyl-phenyl)-ethyl]-methylamide;

and pharmaceutically acceptable salts thereof.

13. A pharmaceutical composition comprising a compound as claimed in claim 1 in a mixture with one or more pharmaceutically acceptable carriers or excipients.

14. A process for preparing a compound according to claim 1, wherein X is CH$_2$ or C(O) and Y is CH$_2$, said process comprising reacting a compound of formula (II):

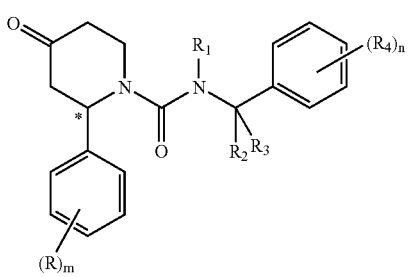

with compound of formula (III):

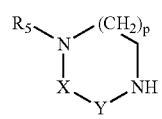

in the presence of a suitable metal reducing agent; followed where necessary or desired by one or more of the following steps:

i) removing any protecting group;
ii) isolating the compound as a salt or thereof; or
iii) separating the compound into enantiomers thereof.

15. A process for preparing a compound according to claim 1, wherein Y is C(O), said process comprising cyclizing a compound of formula (VII),

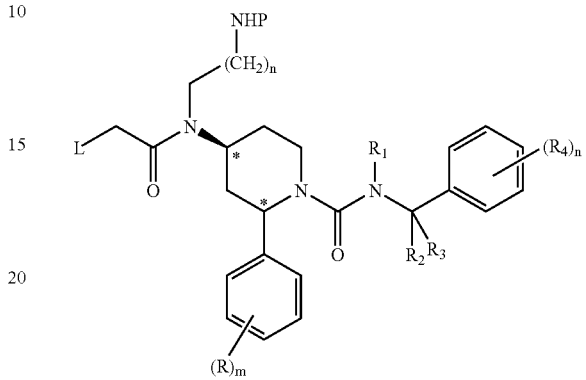

wherein P is a nitrogen protecting group and L is a suitable leaving group; followed where necessary or desired by one or more of the following steps:

i) removing any protecting group;
ii) isolating the compound as a salt or a solvate thereof;
iii) separating the compound into enantiomers thereof.

16. A method for the treatment of a depressive state in a mammal comprising administering an effective amount of a compound as claimed in claim 1.

17. The method according to claim 16 wherein said mammal is man.

18. A method for the treatment of anxiety in a mammal comprising administering an effective amount of a compound as claimed in claim 1.

19. The method according to claim 18 wherein said mammal is man.

20. A method for treatment of emesis in a mammal comprising administering an effective amount of a compound as claimed in claim 1.

21. The method according to claim 20 wherein said mammal is man.

22. A method for treatment of a sleep disorder selected from the group consisting of dysomnia, insomnia, sleep apnea, narcolepsy and circadian rhythmic sleep disorders in a mammal comprising administering an effective amount of a compound as claimed in claim 1.

23. The method according to claim 22 wherein said mammal is man.

* * * * *